US012642914B2

(12) United States Patent

Diaz et al.

(10) Patent No.: US 12,642,914 B2

(45) Date of Patent: Jun. 2, 2026

(54) SYSTEM AND METHOD FOR MICRODOSE INJECTION

(71) Applicant: CREDENCE MEDSYSTEMS, INC., Menlo Park, CA (US)

(72) Inventors: Stephen H. Diaz, Palo Alto, CA (US); Alan E. Shluzas, San Carlos, CA (US)

(73) Assignee: CREDENCE MEDSYSTEMS, INC., Menlo Park, CA (US)

( * ) Notice: Subject to any disclaimer, the term of this patent is extended or adjusted under 35 U.S.C. 154(b) by 605 days.

(21) Appl. No.: 17/888,133

(22) Filed: Aug. 15, 2022

(65) Prior Publication Data

US 2022/0387731 A1 Dec. 8, 2022

Related U.S. Application Data

(63) Continuation of application No. 16/683,126, filed on Nov. 13, 2019, now Pat. No. 11,419,991.

(Continued)

(51) Int. Cl.
*A61M 5/32* (2006.01)
*A61M 5/31* (2006.01)
(Continued)

(52) U.S. Cl.
CPC ........ *A61M 5/3221* (2013.01); *A61M 5/3146* (2013.01); *A61M 5/3148* (2013.01);
(Continued)

(58) Field of Classification Search
CPC .............. A61M 5/315; A61M 5/31501; A61M 5/31565; A61M 5/31576; A61M 5/31578;
(Continued)

(56) References Cited

U.S. PATENT DOCUMENTS 2,736,315 A * 2/1956 Feeney ............. A61M 5/31551
604/242
3,128,765 A * 4/1964 Tint .................. A61M 5/31586
604/232

(Continued)

FOREIGN PATENT DOCUMENTS

JP 2004-148091 A 5/2004
JP 2007-159717 A 6/2007
(Continued)

OTHER PUBLICATIONS

Foreign Response for JP Patent Appln. No. 2019-569308 dated Apr. 12, 2022.

(Continued)

*Primary Examiner* — Bhisma Mehta
*Assistant Examiner* — Mark A Igel
(74) *Attorney, Agent, or Firm* — Vista IP Law Group, LLP

(57) ABSTRACT

In one embodiment, a system for injecting includes a syringe body having proximal and distal ends, a syringe interior, and a syringe flange at the proximal end thereof. The system also includes an injectable fluid disposed in the syringe interior. The system further includes a stopper member disposed in the syringe interior. Moreover, the system includes a plunger member coupled to the stopper member. In addition, the system includes a finger flange removably coupled to the syringe flange, the finger flange including a proximally directed screw. The system also includes a rotatable member disposed on the proximally directed screw, the rotatable member defining a rotatable member opening through which the plunger member is disposed and having an elastic latch disposed adjacent the rotatable member opening.

8 Claims, 21 Drawing Sheets

Related U.S. Application Data

(60) Provisional application No. 62/760,273, filed on Nov. 13, 2018.

(51) Int. Cl.
  *A61M 5/315* (2006.01)
  *A61M 5/34* (2006.01)

(52) U.S. Cl.
  CPC ...... *A61M 5/31526* (2013.01); *A61M 5/3158* (2013.01); *A61M 5/31581* (2013.01); *A61M 5/31595* (2013.01); *A61M 5/347* (2013.01); *A61M 2005/3128* (2013.01); *A61M 2005/3132* (2013.01); *A61M 2005/3152* (2013.01); *A61M 2005/3201* (2013.01); *A61M 2005/3231* (2013.01); *A61M 2005/3241* (2013.01)

(58) Field of Classification Search
  CPC ............ A61M 5/31581; A61M 5/3157; A61M 5/31533; A61M 5/3221; A61M 5/3148; A61M 2005/3128; A61M 2005/3132; A61M 2005/3152; A61M 2005/3201; A61M 2005/3231; A61M 2005/3241
  See application file for complete search history.

(56) References Cited

U.S. PATENT DOCUMENTS

| | | | | |
|---|---|---|---|---|
| 4,583,978 | A * | 4/1986 | Porat | A61M 5/31551 604/218 |
| 4,710,179 | A * | 12/1987 | Haber | A61M 5/31595 604/211 |
| 5,271,527 | A * | 12/1993 | Haber | A61M 5/24 222/137 |
| 5,433,352 | A * | 7/1995 | Ronvig | A61M 5/31595 604/209 |
| 6,126,644 | A * | 10/2000 | Naganuma | A61F 9/007 604/232 |
| 8,932,268 | B1 * | 1/2015 | Struzinski | A61M 5/3137 604/218 |
| 9,345,842 | B2 * | 5/2016 | Chanoch | A61M 5/31561 |
| 11,090,445 | B2 | 8/2021 | Diaz et al. | |
| 2002/0183698 | A1 * | 12/2002 | Quinn | A01K 11/00 604/227 |
| 2003/0032928 | A1 | 2/2003 | Sudo et al. | |
| 2006/0206057 | A1 * | 9/2006 | DeRuntz | A61M 5/31551 604/224 |
| 2007/0265579 | A1 * | 11/2007 | Kleyman | A61C 5/62 604/207 |
| 2008/0221530 | A1 * | 9/2008 | Glejbol | A61M 5/31551 604/211 |
| 2011/0046559 | A1 * | 2/2011 | Lum | A61M 5/3135 604/218 |
| 2011/0190709 | A1 | 8/2011 | Mitsuno et al. | |
| 2013/0226091 | A1 * | 8/2013 | Nzike | A61M 5/31533 604/131 |
| 2013/0245566 | A1 * | 9/2013 | De Sausmarez Lintell | A61M 5/3156 604/246 |
| 2016/0045673 | A1 * | 2/2016 | Bayer | A61M 5/31583 604/209 |
| 2016/0220761 | A1 * | 8/2016 | Shetty | A61M 5/20 |
| 2016/0228643 | A1 * | 8/2016 | Oberdorfer | A61M 5/3137 |
| 2016/0263329 | A1 * | 9/2016 | Young | A61M 5/31528 |
| 2016/0293329 | A1 | 10/2016 | Sagawa et al. | |
| 2019/0015597 | A1 * | 1/2019 | Holmqvist | A61M 5/178 |
| 2019/0344021 | A1 * | 11/2019 | Shluzas | A61M 5/322 |
| 2020/0306453 | A1 * | 10/2020 | Langley | A61M 5/31558 |
| 2020/0324054 | A1 * | 10/2020 | Helmer | A61M 5/3158 |

FOREIGN PATENT DOCUMENTS

| | | |
|---|---|---|
| JP | B 4675537 | 4/2011 |
| JP | S 49-18460 Y | 4/2012 |
| JP | 2012-231932 | 11/2012 |
| JP | 2015-500095 | 1/2015 |
| JP | 2016-537108 | 12/2016 |
| WO | WO 2009/154107 | 12/2009 |
| WO | WO 2018/146589 | 8/2018 |
| WO | WO-2018146589 A2 * | 8/2018 ........ A61M 5/31585 |

OTHER PUBLICATIONS

Foreign NOA for JP Patent Appln. No. 2019-569308 dated Apr. 18, 2022 (with English translation).
Foreign OA for JP Patent Appln. No. 2022-100018 dated Aug. 8, 2023 (with English translation).
Foreign OA for JP Patent Appln. No. 2021-525106 dated Feb. 7, 2023 (with English translation).
Foreign Response for JP Patent Appln. No. 2021-525106 dated Jul. 7, 2023.
Non-Final Office Action for U.S. Appl. No. 17/403,095 dated Aug. 14, 2023.
Ex Parte Quaye Action for U.S. Appl. No. 17/351,006 dated Jun. 16, 2023.
Amendment Response to Ex Parte Quayle for U.S. Appl. No. 17/351,006 dated Aug. 15, 2023.
Notice of Allowance for U.S. Appl. No. 17/351,006 dated Aug. 23, 2023.
Notice of Allowance for U.S. Appl. No. 17/351,006 dated Sep. 13, 2023.
Foreign Response to JP Patent Appln. No. 2022-100018 dated Oct. 3, 2023.
Amendment Response to NFOA for U.S. Appl. No. 17/403,095 dated Nov. 14, 2023.
Foreign Exam Report for EP Patent Appln. No. 18738167.8 dated Nov. 15, 2022.
Foreign Response for EP Patent Appln. No. 18738167.8 dated Mar. 27, 2023.
Foreign OA for JP Patent Appln. No. 2021-525106 dated Sep. 26, 2023.
Notice of Allowance for U.S. Appl. No. 17/403,095 dated Dec. 15, 2023.
Foreign OA to JP Patent Appln. No. 2022-100018 dated Jan. 12, 2024 (with English translation).
Foreign OA Response for JP Patent Appln. No. 2021-525106 dated Dec. 26, 2023.
Foreign Voluntary Amendment for CA Patent Appln. No. 3119277 dated Dec. 21, 2023.
Foreign NOA for CA Patent Appln. No. 3119277 dated Jan. 25, 2024.
Foreign Response to Exam Report for CA Patent Appln. No. 3067225 dated Apr. 11, 2024.
Foreign OA for JP Patent Appln. No. 2022-100018 dated Feb. 27, 2024.
Foreign Response to JP Patent Appln. No. 2022-100018 dated Apr. 10, 2024.
Foreign NOA for JP Patent Appln. No. 2022-100018 dated May 7, 2024 (with English translation).
Foreign NOA for JP Patent Appln. No. 2021-525106 dated Mar. 26, 2024 (with English translation).
Foreign NOA for CA Patent Appln. No. 3067225 dated Jun. 12, 2024.
Foreign OA for EP Patent Appln. No. 19817493.0 dated Jun. 13, 2024.
Foreign OA Response for EP Patent Appln. No. 19817493.0 dated Oct. 14, 2024.
Foreign OA for JP Patent Appln. No. 2024-091165 dated Apr. 8, 2025 (with English translation).
Foreign OA Response for JP Patent Appln. No. 2024-091165 dated Jun. 30, 2025.
Foreign OA for JP Patent Appln. No. 2024-030326 dated Mar. 11, 2025 (with English translation).
Notice of Allowance for U.S. Appl. No. 18/638,893 dated Apr. 9, 2025.
Foreign NOA for EP Patent Appln. No. 18 738 167.8 dated May 7, 2025.

(56)     References Cited

OTHER PUBLICATIONS

Foreign NOA for JP Patent Appln. No. 2024-091165 dated Aug. 8, 2025 (with English translation).

Foreign Response for JP Patent Appln. No. 2024-070326 dated Jun. 4, 2025.

Notice of Allowance for U.S. Appl. No. 18/421,046 dated Oct. 7, 2025.

Extended European Search Report for EP Patent Appln. No. 25200836.2 dated Oct. 27, 2025.

Foreign Decision of Rejection for JP Patent Appln. No. 2024-070326 dated Oct. 23, 2025 (with English translation).

Foreign Response for JP Patent Appln. No. 2024-070326 dated Jan. 28, 2026.

* cited by examiner

*14*

*12*

*16*

*18*

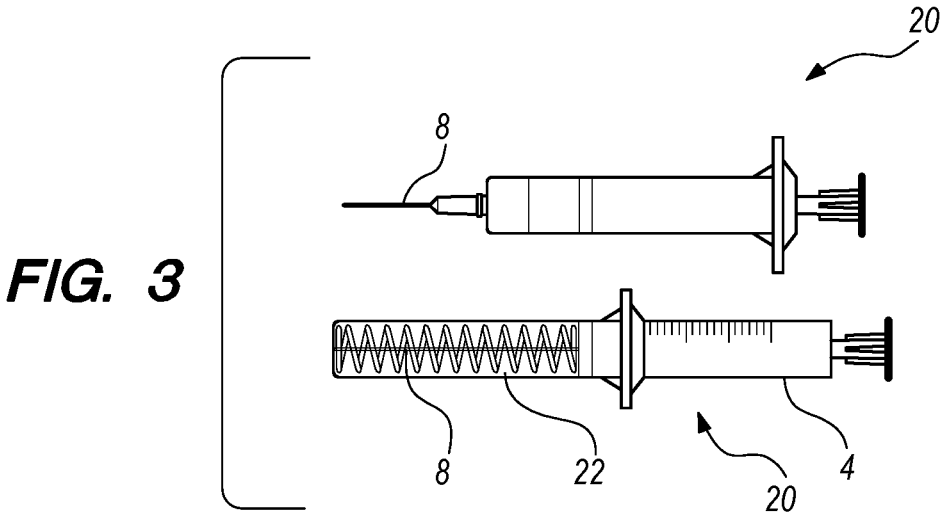
*FIG. 3*
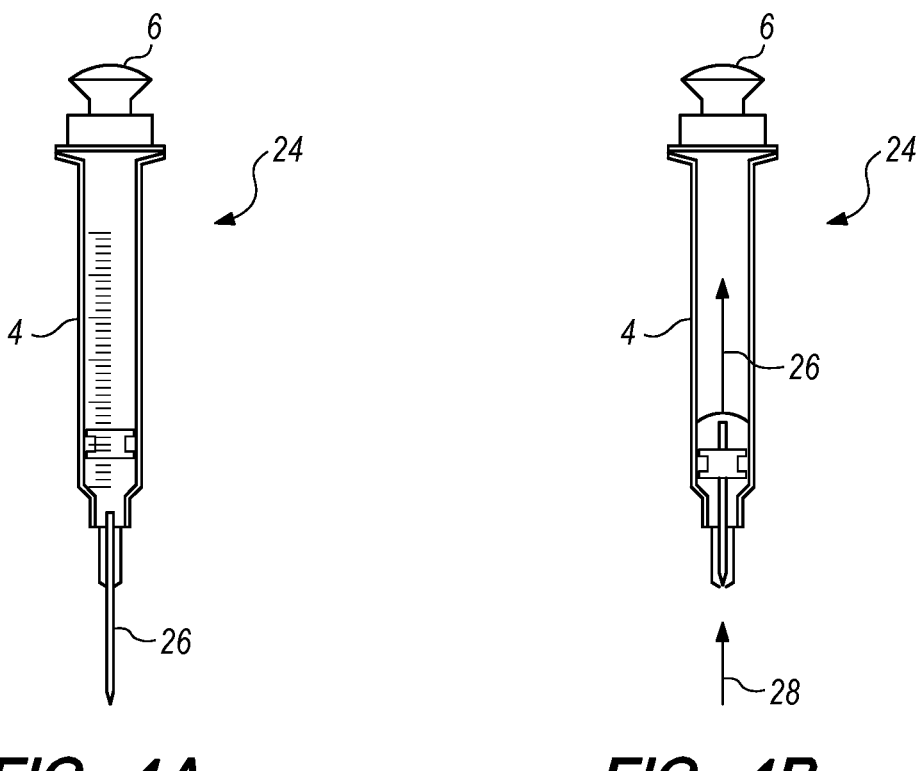
*FIG. 4A*            *FIG. 4B*

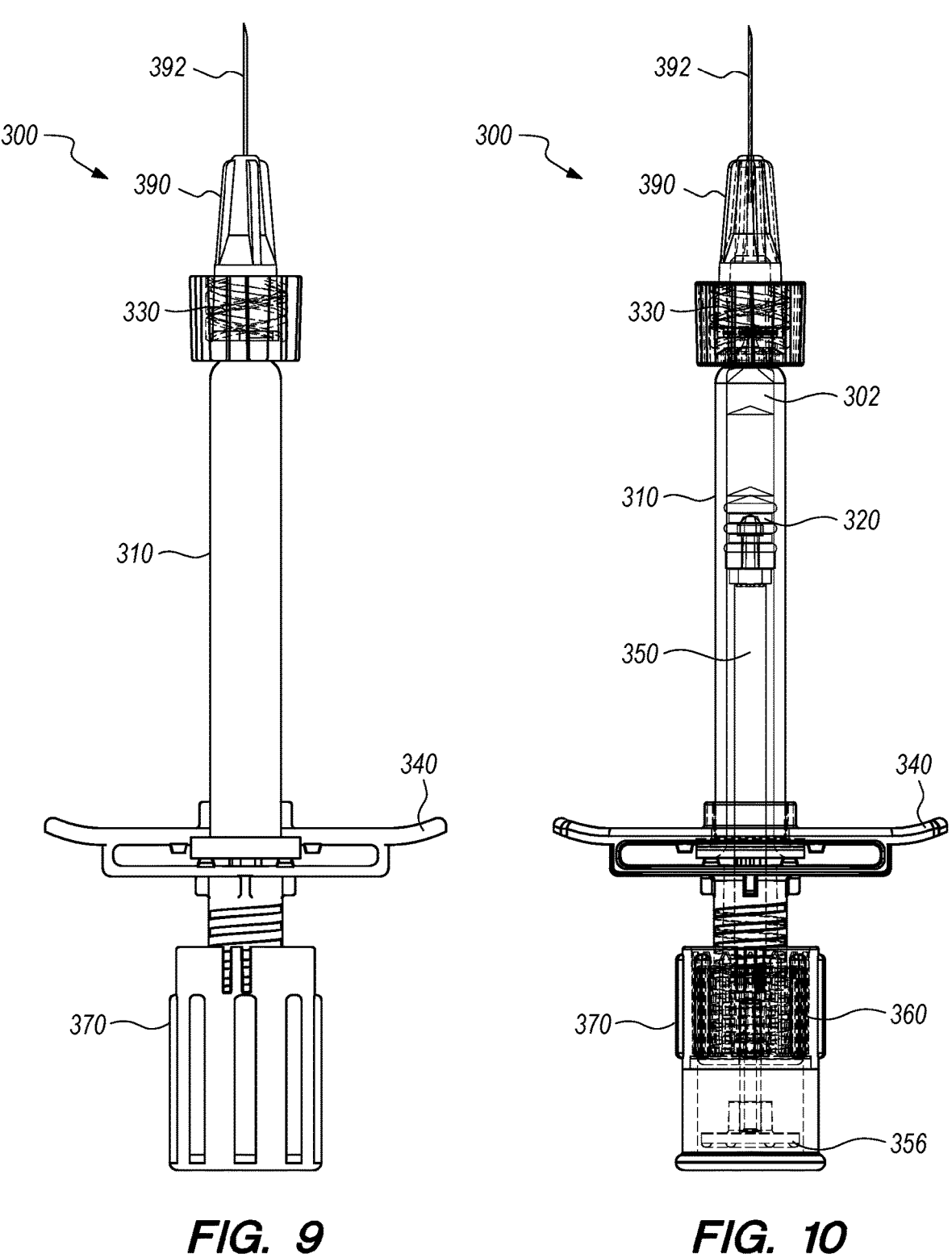
FIG. 9          FIG. 10

1

SYSTEM AND METHOD FOR MICRODOSE INJECTION

The present application is a continuation of U.S. patent application Ser. No. 16/683,126 filed on Nov. 13, 2019 entitled "SYSTEM AND METHOD FOR MICRODOSE INJECTION", which claims priority to (1) U.S. Provisional Patent Application Ser. No. 62/760,273, filed on Nov. 13, 2018, and entitled "SYSTEM AND METHOD FOR SAFETY SYRINGE." This application also includes subject matter similar to the subject matter described in the following co-owned U.S. patent applications: (2) Ser. No. 14/696, 342, filed Apr. 24, 2015, and entitled "SYSTEM AND METHOD FOR SAFETY SYRINGE"; (3) Ser. No. 14/543, 787, filed Nov. 17, 2014, and entitled "SYSTEM AND METHOD FOR DRUG DELIVERY WITH A SAFETY SYRINGE"; (4) Ser. No. 14/321,706, filed Jul. 1, 2014, and entitled "SAFETY SYRINGE"; and (5) Ser. No. 62/416, 102, filed Nov. 1, 2016, and entitled "SYSTEM AND METHOD FOR SAFETY SYRINGE"; (6) Ser. No. 62/431, 382, filed Dec. 7, 2016, and entitled "SYSTEM AND METHOD FOR SAFETY SYRINGE"; (7) Ser. No. 62/480, 276, filed Mar. 31, 2017, and entitled "SYSTEM AND METHOD FOR SAFETY SYRINGE; (8) Ser. No. 62/508, 508, filed May 19, 2017, and entitled "SYSTEM AND METHOD FOR COLLECTING INJECTION INFORMA-TION"; (9) Ser. No. 62/542,230, filed Aug. 7, 2017, and entitled "CARTRIDGE SAFETY INJECTION SYSTEM AND METHODS"; (10) Ser. No. 15/801,239, filed Nov. 1, 2017, and entitled "SYSTEM AND METHOD FOR SAFETY SYRINGE"; (11) Ser. No. 15/801,259, filed Nov. 1, 2017, and entitled "SYSTEM AND METHOD FOR SAFETY SYRINGE"; (12) Ser. No. 15/801,281, filed Nov. 1, 2017, and entitled "CARTRIDGE SAFETY INJECTION SYSTEM AND METHODS"; (13) Ser. No. 15/801,304, filed Nov. 1, 2017, and entitled "SYSTEM AND METHOD FOR SAFETY SYRINGE"; (14) Ser. No. 16/011,453, filed Jun. 18, 2018, and entitled "SYSTEM AND METHOD FOR SAFETY SYRINGE"; and (15) Ser. No. 15/985,354, filed May 21, 2018, and entitled "SYSTEM AND METHOD FOR COLLECTING INJECTION INFORMATION", "(16) Ser. No. 16/683,157, filed Nov. 13, 2019, and entitled "SYSTEM AND METHOD FOR MULTIPLE SITE INJEC-TION". The contents of the above-mentioned applications are fully incorporated herein by reference as though set forth in full.

FIELD OF THE INVENTION

The present invention relates generally to injection sys-tems, devices, and processes for facilitating various levels of control over fluid infusion, and more particularly to systems and methods related to syringes for delivery microliter range doses of fluids in healthcare environments.

BACKGROUND

Millions of syringes, such as that depicted in FIG. 1A 2, are consumed in healthcare environments every day. A typical syringe 2 includes a tubular body 4, a plunger 6, and an injection needle 8. As shown in FIG. 1B, such a syringe 2 may be utilized not only to inject fluid into a patient, but also to withdraw or expel fluid out of or into a container such as a medicine bottle, vial, bag, or other drug containment system 10. Indeed, due to regulatory constraints in some countries such as the United States as well as sterility maintenance concerns, upon use of a medicine bottle 10 with a syringe 2 as shown in a particular patient's environment, such medicine bottle may only be utilized with a single patient and then must be disposed of—causing significant medical waste from bottle and remaining medicine disposal, and even contributing to periodic shortages of certain critical drugs.

Referring to FIG. 2A, three Luer-type syringes 12 are depicted, each having a Luer fitting geometry 14 disposed distally, so that they may be coupled with other devices having similar mating geometry, such as the Luer manifold assembly 16 depicted in FIG. 2B. The Luer manifold assem-bly of FIG. 2B may be used to administer liquid drugs to the patient intravenously with or without the use of an intrave-nous infusion bag. The Luer fittings 14 of the syringes of FIG. 2A may be termed the "male" Luer fittings, while those of FIG. 2B 18 may be termed the "female" Luer fittings; one of the Luer interfaces may be threaded (in which case the configuration may be referred to as a "Luer lock" configu-ration) so that the two sides may be coupled by relative rotation, which may be combined with compressive loading. In other words, in one Luer lock embodiment, rotation, possibly along with compression, may be utilized to engage threads within the male fitting 14 which are configured to engage a flange on the female fitting 18 and bring the devices together into a fluid-sealed coupling. In another embodiment, tapered interfacing geometries may be utilized to provide for a Luer engagement using compression with-out threads or rotation (such a configuration may be referred to as a "slip-on" or "conical" Luer configuration). While such Luer couplings are perceived to be relatively safe for operators, there is risk of medicine spilling/leaking and parts breakage during the loading to provide a Luer coupling. The use of needle injection configurations, on the other hand, carries with it the risk of a sharp needle contacting or poking a person or structure that is not desired. For this reason, so called "safety syringes" have been developed.

One embodiment of a safety syringe 20 is shown in FIG. 3, wherein a tubular shield member 22 is spring biased to cover the needle 8 when released from a locked position relative to the syringe body 4. Another embodiment of a safety syringe 24 is shown in FIGS. 4A-4B. With such a configuration, after full insertion of the plunger 6 relative to the syringe body 4, the retractable needle 26 is configured to retract 28, 26 back to a safe position within the tubular body 4, as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity con-trol which may be associated with pain and patient anxiety.

Further complicating the syringe marketplace is an increasing demand for pre-filled syringe assemblies such as those depicted in FIGS. 5A and 5B, which generally include a syringe body, or "drug enclosure containment delivery system", 34, a plunger tip, plug, or stopper 36, and a distal seal or cap 35 which may be fitted over a Luer type interface (FIG. 5A shows the cap 35 in place; FIG. 5B has the cap removed to illustrate the Luer interface 14. Liquid medicine may reside in the volume, or medicine reservoir, 40 between the distal seal 35 and the distal end 37 of the stopper member 36. The stopper member 36 may include a standard butyl rubber material and may be coated, such as with a biocom-patible lubricious coating (e.g., polytetrafluoroethylene ("PTFE")), to facilitate preferred sealing and relative motion characteristics against the associated syringe body 34 structure and material. The proximal end of the syringe body 34 in FIG. 5B includes a conventional integral syringe flange 38), which is formed integral to the material of the syringe body 34. The flange 38 is configured to extend radially from the syringe body 34 and may be configured to be a full circumference, or a partial circumference around the syringe body 34. A partial flange is known as a "clipped flange" while the other is known as a "full flange." The flange is used to grasp the syringe with the fingers to provide support for pushing on the plunger to give the injection. The syringe body 34 preferably includes a translucent material such as a glass or polymer. To form a contained volume within the medicine chamber or reservoir 40, and to assist with expulsion of the associated fluid through the needle, a stopper member 36 may be positioned within the syringe body 34. The syringe body may define a substantially cylindrical shape (i.e., so that a plunger tip 36 having a circular cross sectional shape may establish a seal against the syringe body), or be configured to have other cross sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that 41 featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

Moreover, injection systems have reduced accuracy and precision as the volume of injectable fluid is reduced into the microliter range ("microdose"). In particular, removing air from the syringe body ("de-bubbling") before injection is difficult to perform accurately and precisely for such microdose injection systems.

There is a need for injection systems which address shortcomings of currently-available configurations. In particular, there is a need for injection systems that perform (de-bubble and inject) accurately in the microliter range. It is also desirable that such syringe assemblies may utilize the existing and relatively well-controlled supply chain of conventionally delivered pre-filled cartridges and other off-the-shelf components, and the corresponding assembly machinery and personnel.

SUMMARY

Embodiments are directed to injection systems. In particular, the embodiments are directed to microliter range injection systems that include at least some off-the-shelf syringe components.

In one embodiment, a system for injecting includes a syringe body having proximal and distal ends, a syringe interior, and a syringe flange at the proximal end thereof. The system also includes an injectable fluid disposed in the syringe interior. The system further includes a stopper member disposed in the syringe interior. Moreover, the system includes a plunger member coupled to the stopper member. In addition, the system includes a finger flange removably coupled to the syringe flange, the finger flange including a proximally directed screw. The system also includes a rotatable member disposed on the proximally directed screw, the rotatable member defining a rotatable member opening through which the plunger member is disposed and having an elastic latch disposed adjacent the rotatable member opening. The rotatable member is configured to insert the plunger member and the stopper member coupled thereto distally in the syringe interior relative to the syringe body with rotation of the rotatable member relative to the proximally directed screw. The elastic latch is configured to allow the plunger member to be inserted distally through the rotatable member opening while preventing removal of the plunger member proximally from the rotatable member through the rotatable member opening.

In one or more embodiments, the syringe body also includes a distal needle interface configured to be coupled to a needle assembly having a needle. Rotating the rotatable member may insert the plunger member and the stopper member, thereby forcing a portion of the injectable fluid from the syringe interior through the needle to prime the needle for injection.

In one or more embodiments, the plunger member includes a thumbpad at a proximal end thereof, and the system also includes a plunger cap removably coupled to the rotatable member and configured to prevent a user from contacting the thumbpad. The rotatable member may define a slanted trough and a circumferential trough on an exterior surface thereof, and the plunger cap may include a tang inwardly directed toward a longitudinal axis of the plunger cap. When the tang is disposed in the circumferential trough, an interference between the tang and the circumferential trough may prevent proximal movement of the plunger cap relative to the rotatable member. The rotatable member may also include a bump disposed on the exterior surface thereof between the slanted trough and the circumferential trough. The bump on the rotatable member and the tang on the plunger cap may be configured to prevent the plunger cap from disengaging from the rotatable member until a predetermined amount of torque is applied to the plunger cap relative to the rotatable member. The predetermined amount of torque may be selected such that the plunger cap disengages from the rotatable member only after the rotatable member reaches a distal end of the proximally directed screw on the finger flange, thereby forcing a portion of the injectable fluid the syringe interior through the needle to prime the needle for injection.

In one or more embodiments, the plunger cap defines a proximal opening sized to allow the plunger member to pass therethrough. The plunger member may include a flange configured to interfere with the elastic latch to limit proximal movement of the plunger member relative to the rotatable member. The rotatable member may include a thread end disposed at a distal end thereof, and the finger flange may include a latch disposed on proximally directed screw and configured to interfere with the thread end to limit rotation and proximal movement of the rotatable member relative to the finger flange.

In another embodiments, a method for assembling a system for injecting includes coupling a rotatable member to a finger flange to form a finger flange/rotatable member unit. The method also includes coupling a plunger cap to the rotatable member to form a finger flange/rotatable member/plunger cap unit. The method further includes mounting the finger flange/rotatable member/plunger cap unit onto a pre-filled syringe. The pre-filled syringe includes a syringe body defining a syringe interior, an injectable fluid disposed in the syringe interior, and a stopper member disposed in the syringe interior and retaining the injectable fluid in the syringe interior. Moreover, the method includes inserting a plunger member through the finger flange/rotatable member/plunger cap unit into the syringe interior. In addition, the method includes coupling the plunger member to the stopper member in the syringe interior.

In one or more embodiments, the finger flange includes a proximally directed screw, and the method also includes coupling the rotatable member to the finger flange to form the finger flange/rotatable member unit by twisting the rotatable member onto the proximally directed screw on the finger flange.

In one or more embodiments, the plunger cap defines a proximal opening, the rotatable member defines a rotatable member opening, and the finger flange defines a finger flange opening. The method also includes inserting the plunger member through the proximal opening, the rotatable member opening, and the finger flange opening into the syringe interior. The rotatable member may define a slanted trough and a circumferential trough on an exterior surface thereof. The plunger cap may include a tang inwardly directed toward a longitudinal axis of the plunger cap. The method may also include coupling the plunger cap to the rotatable member to form the finger flange/rotatable member/plunger cap unit by twisting the plunger cap onto the rotatable member such that the tang in the plunger cap is disposed in the circumferential trough and an interference between the tang and the circumferential trough prevents proximal movement of the plunger cap relative to the rotatable member.

In one or more embodiments, the finger flange includes a side opening, and where the syringe body includes a syringe flange. The method also includes mounting the finger flange/rotatable member/plunger cap unit onto the syringe body by inserting the syringe flange of the syringe body into the side opening of the finger flange. The stopper member may include a threaded stopper member recess, and the plunger member may include distal threaded member. The method may also include coupling the plunger member to the stopper member in the syringe interior by twisting the distal threaded member of the plunger member into the threaded stopper member recess of the stopper member.

In still another embodiment, a method for injecting a fluid includes providing a syringe assembly. The syringe assembly includes a syringe body having proximal and distal ends, a syringe interior, a distal needle interface at the distal end thereof, and a syringe flange at the proximal end thereof. The syringe assembly also includes an injectable fluid disposed in the syringe interior. The syringe assembly further includes a stopper member disposed in the syringe interior. Moreover, the syringe assembly includes a plunger member coupled to the stopper member. In addition, the syringe assembly includes a finger flange removably coupled to the syringe flange, the finger flange including a proximally directed screw. The syringe assembly also includes a rotatable member disposed on the proximally directed screw. The syringe assembly further includes a plunger cap removably coupled to the rotatable member. Moreover, the syringe assembly includes a needle assembly having a needle coupled to the distal needle interface of the syringe body. The method also includes rotating the plunger cap relative to the proximally directed screw to rotate the rotatable member relative to the proximally directed screw to thereby force a portion of the injectable fluid from the syringe interior through the needle to prime the needle for injection. The method further includes removing the plunger cap from the rotatable member to thereby expose a proximal end of the plunger member.

Moreover, the method includes applying a distally directed force to the proximal end of the plunger member to expel another portion of the injectable fluid from the syringe interior through the needle.

In one or more embodiments, the rotatable member defines a slanted trough and a circumferential trough on an exterior surface thereof and includes a bump disposed on the exterior surface thereof between the slanted trough and the circumferential trough. The plunger cap may include a tang inwardly directed toward a longitudinal axis of the plunger cap. When the tang is disposed in the circumferential trough, an interference between the tang and the circumferential trough may prevent proximal movement of the plunger cap relative to the rotatable member. The bump on the rotatable member and the tang on the plunger cap may be configured to prevent the plunger cap from disengaging from the rotatable member until a predetermined amount of torque is applied to the plunger cap relative to the rotatable member. Removing the plunger cap from the rotatable member may include applying the predetermined amount of torque to the plunger cap relative to the rotatable member after the rotatable member reaches a distal end of the proximally directed screw on the finger flange.

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein:

FIGS. 1A-5C illustrate various aspects of conventional injection syringe configurations.

FIGS. 6-20 illustrate various aspects of a microdose injection system and a microdose injection method according to some embodiments.

Figure 1A:
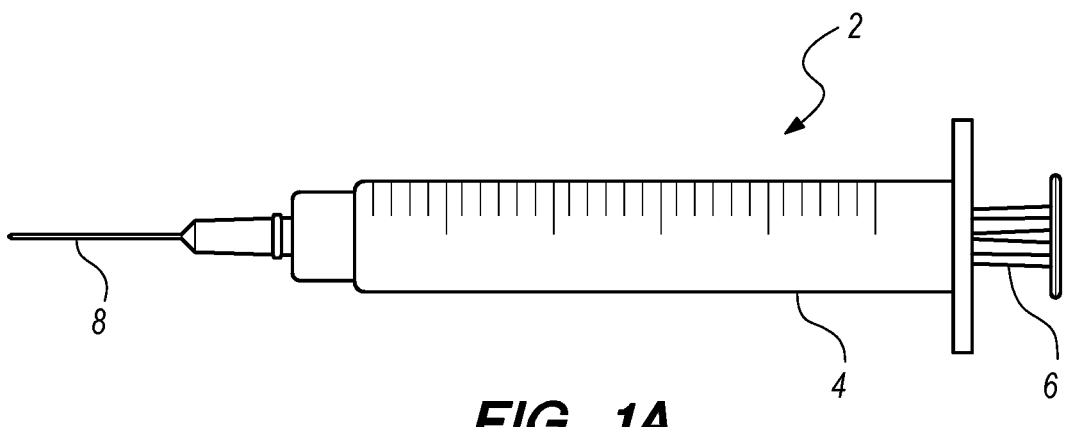
Figure 1B:
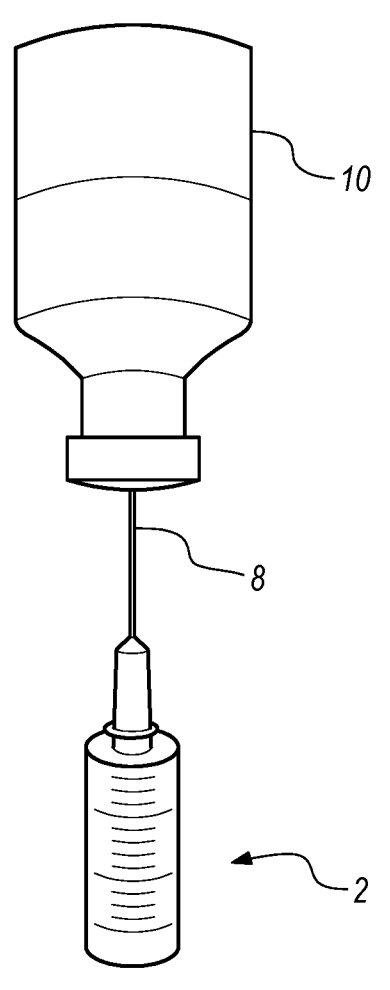
Figure 2A:
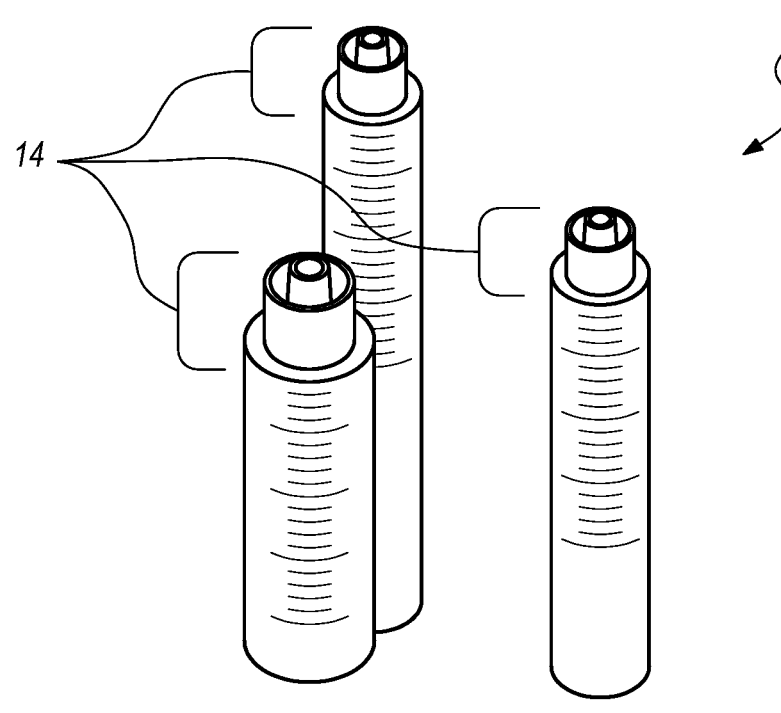
Figure 2B:
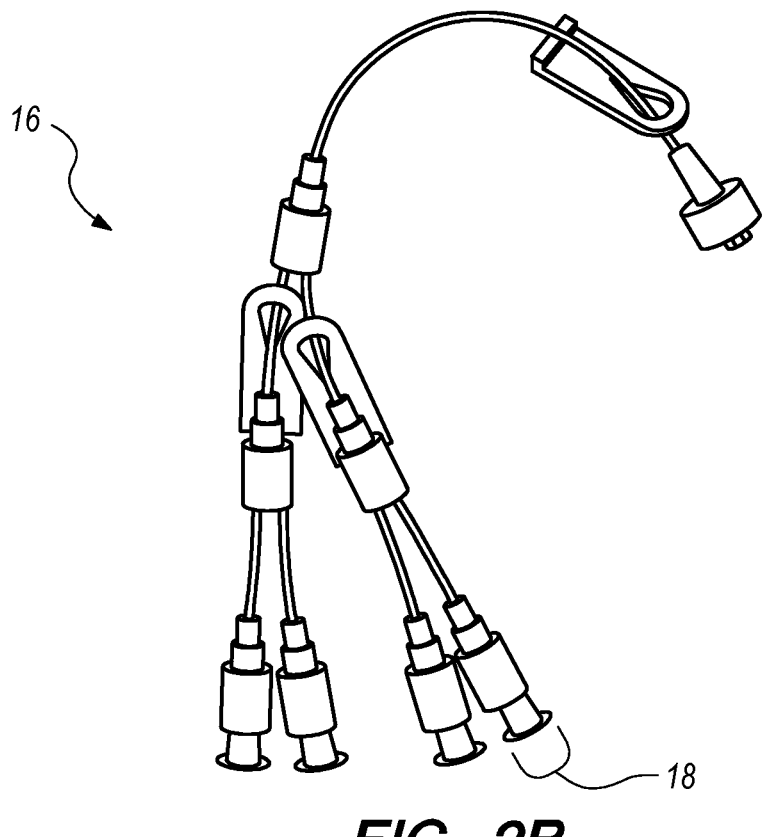
Figure 5A:
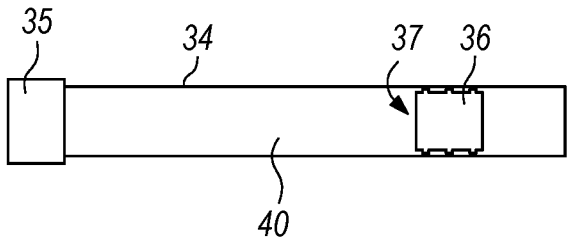
Figure 5B:
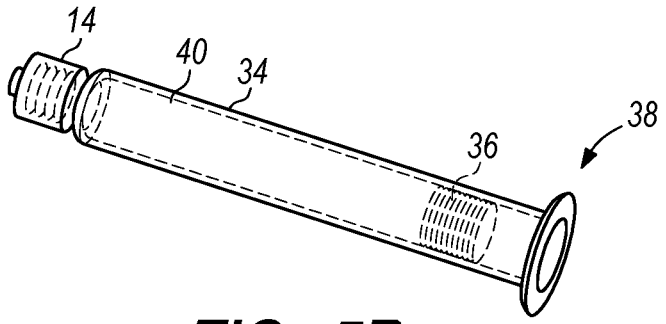
Figure 5C:
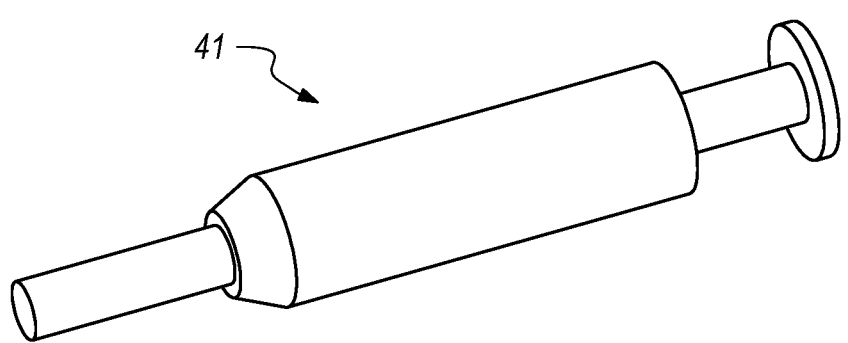

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Microdose Injection System

FIGS. 6-20 depict a microdose injection system 300 according to another embodiment. As used herein, the term "microdose" or "micro-dose" includes, but is not limited to, injections in the 1-1,000 microliter range. The microdose injection system 300 addresses the problem of injections in the microliter (e.g., 10 μL) volume range, which are difficult to accomplish with a standard injection system while maintaining precision (e.g., repeatability) and accuracy (e.g., proximity to desired volume). The microdose injection system 300 utilizes a rotatable microdose adapter/rotatable member 360 and a fixed plunger member travel distance/gap to perform microdose injections.

Like many of the injection systems described in co-owned U.S. patent application Ser. Nos. 14/696,342, 14/543,787, 14/321,706, 62/416,102, 62/431,382, 62/480,276, 62/508, 508, 62/542,230, Ser. Nos. 15/801,239, 15/801,259, 15/801, 281, 15/801,304, 16/011,453, the contents of which were previously fully incorporated herein by reference as though set forth in full, the microdose injection system 300 utilizes off-the-shelf syringe bodies 310, stopper members 320, and connection members 330. The microdose injection system 300 may also use off-the-shelf needles assemblies 390 including needles 392. The finger flange 340 in the micro-dose injection system 300 includes a male threaded proximal section 342 configured to mate with a microdose adapter/rotatable member 360 having corresponding female threads, as shown in FIGS. 11, 14, 17, and 20.

The microdose injection system 300 includes a syringe body 310, a stopper member 320, a connection member 330, a finger flange 340, a plunger member 350, a needle assembly 390, and a microdose adapter/rotatable member 360. Many of these system components (e.g., the syringe body 310, the stopper member 320, and the connection member 330) may be off-the-shelf components to utilize the existing and relatively well-controlled supply chain, and the corresponding assembly machinery and personnel. The syringe body 310 may be an off-the-shelf 0.50 cc syringe body 310 to improve the accuracy of the microdose injection system 300. The needle assembly 390 may be a commercially available, off-the-shelf needle assembly with a needle 392 (e.g., 20-34 gauge and length 6 mm-⅝"; in particular 32 gauge×6 mm length). The needle assembly 390 may utilize Luer lock or Luer slip configurations to attach the needle assembly 390 to the syringe body 310/connection member 330. In some embodiments, microdose injection systems 300 can achieve error rates of less than ±10 μL.

The microdose adapter/rotatable member 360 includes a flange 362 configured to exert a small distal force on the shoulder/internal stop 352 formed on the plunger member 350 when the microdose adapter/rotatable member 360 is rotated clockwise onto the male threaded proximal section 342 of the finger flange 340. Rotating the microdose adapter/rotatable member 360 with the microdose injection system 300 in a vertical orientation can remove bubbles ("de-bubble" or "de-gassing") from an injectable substance in the syringe interior 312 and/or an interior of the needle assembly 390/needle 392.

Further, the plunger member 350 includes a narrow portion 354 configured to pass through an opening 364 in the microdose adapter/rotatable member 360, which is sur-rounded by/expands to form the shoulder/internal stop 352. The length of the narrow portion 354 can be modified to control the injection volume and travel distance/gap.

The microdose injection system 300 depicted in FIGS. 6-20 also includes a plunger cap 370. The plunger cap 370 is configured to prevent premature injection by preventing distal movement of the plunger member 350, while allowing the microdose adapter/rotatable member 360 to rotate to the de-bubble the microdose injection system 300. After the plunger cap 370 is removed, the plunger member 350 can be moved distally, but only a length equal to a length of the narrow portion 354 outside of the microdose adapter/rotat-able member 360, which is equal to the travel distance/gap. Therefore, the injection volume is controlled by this length of the narrow portion 354. The microdose injection system 300 can therefore give precise and accurate injections with a precision de-bubbling mechanism.

Figures 6, 7:
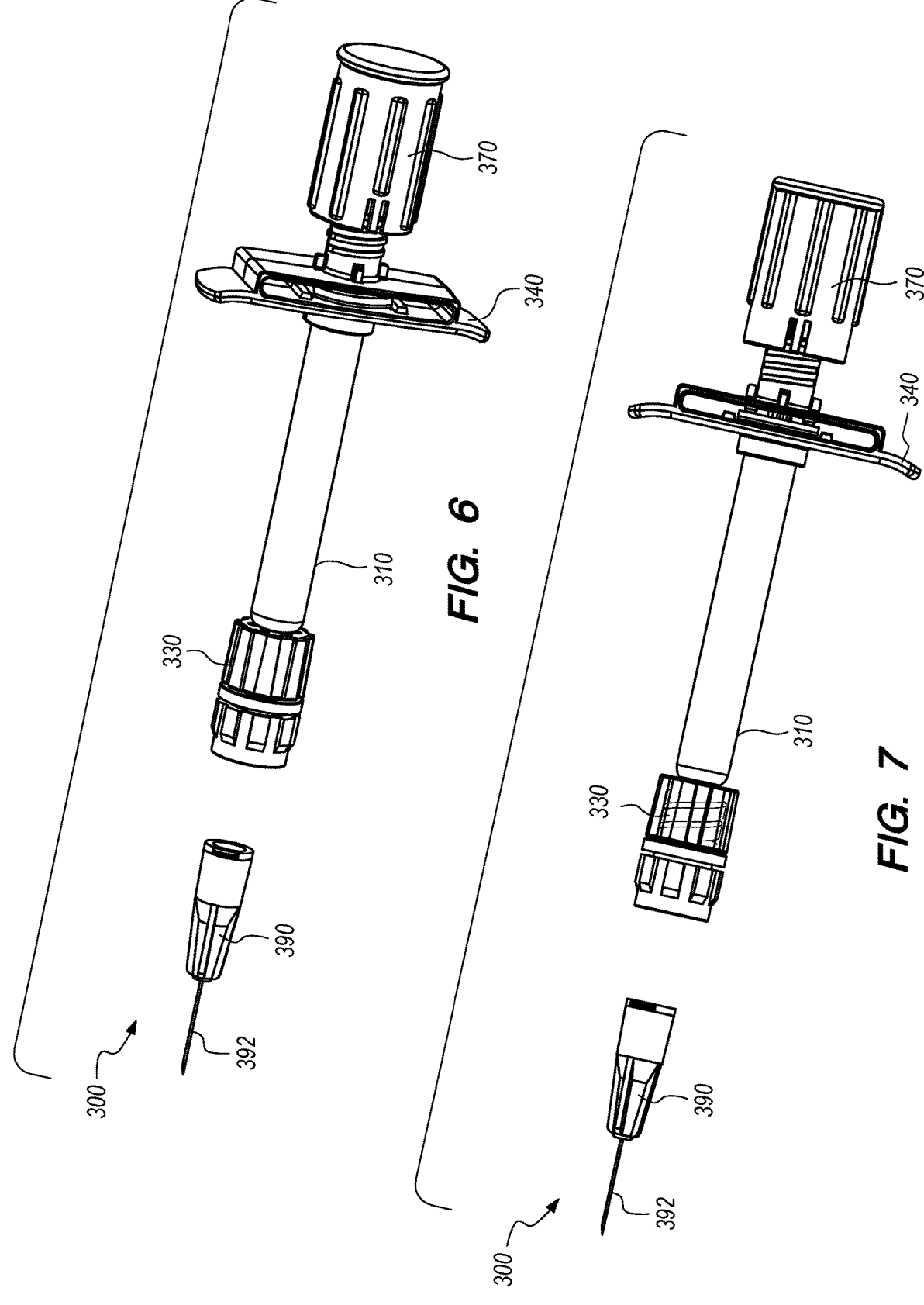
Figure 8:
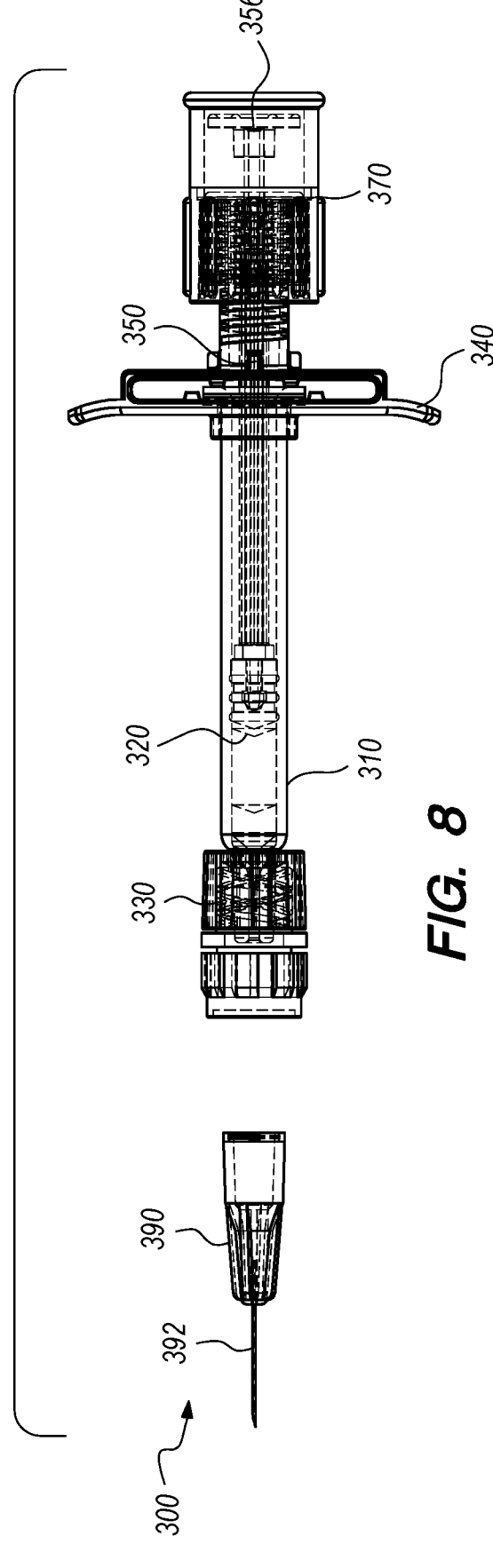

FIGS. 6-20 depict an injection process using the micro-dose injection system 300. FIGS. 6-8 depict the microdose injection system 300 before it is coupled to a needle using the connection member 330. In this state, the connection member 330 is capped by a connection member cover.

Figure 11:
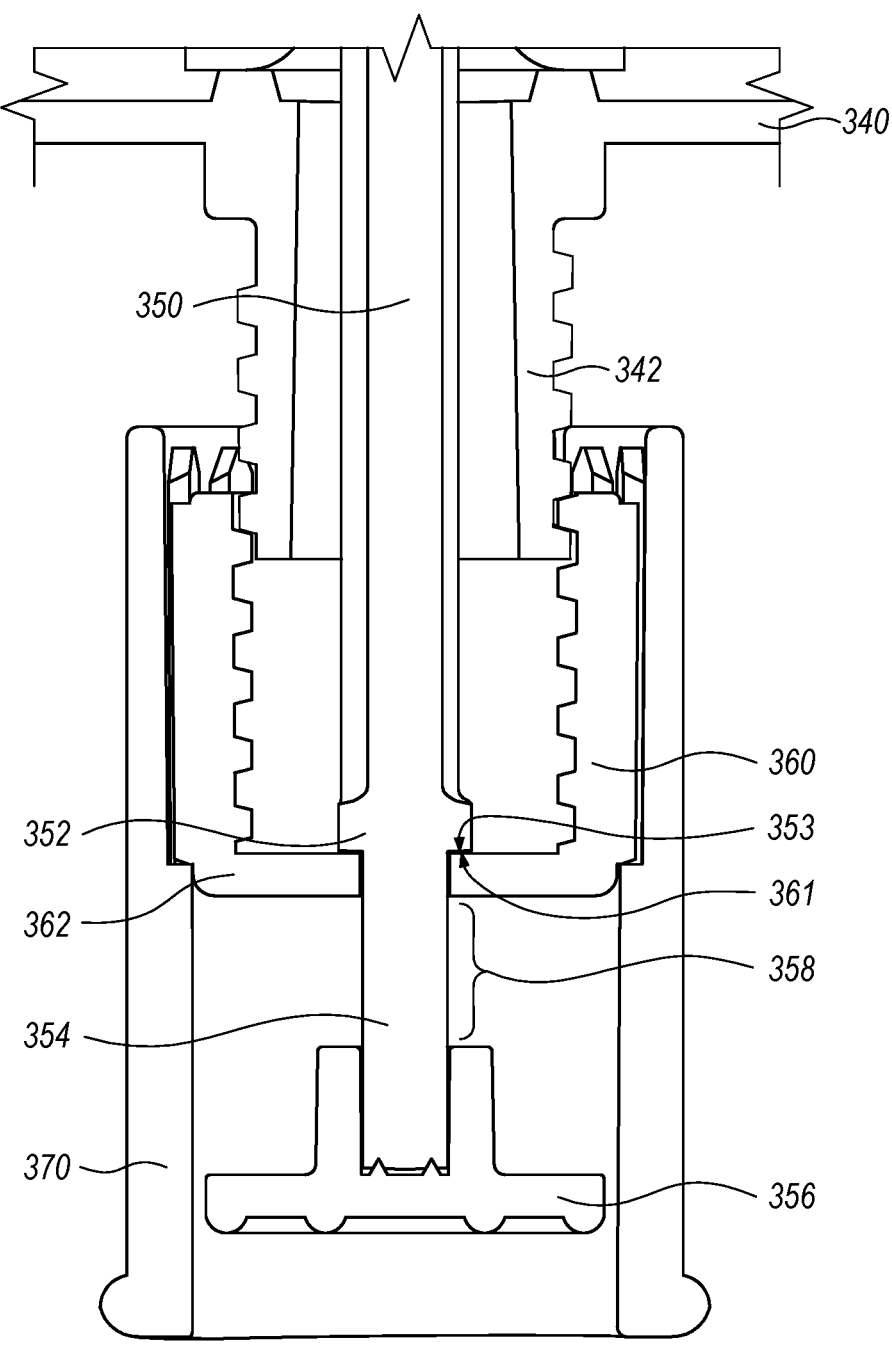

FIGS. 9-11 depict the microdose injection system 300 after the needle has been coupled to the microdose injection system 300 using the connection member 330. In this embodiment, the connection member 330 is a female Luer connector, and the corresponding connection member on the needle is a male Luer connector, resulting in a Luer lock connection, as shown in FIG. 10.

FIGS. 9-11 depict the microdose injection system 300 in a vertical position, wherein the needle is pointed generally upward. This causes any gas/air in the syringe body 310 to move to the top of the syringe body 310 as shown by the gas/air bubble 302 in FIG. 10. In this position, distal movement of the stopper member 320 will eject the gas/air bubble 302 from the syringe body 310 and/or eject air from an interior of the needle assembly 390/needle 392, thereby preparing the microdose injection system 300 for injection. The process of ejecting the gas/air bubble 302 from the syringe body 310 and/or ejecting air from the interior of the needle assembly 390/needle 392 is also referred to as de-bubbling or priming the injection system 300 for use. The process of priming the injection system may also eject a portion of the injectable fluid from the syringe or from the needle.

FIG. 11 depicts in detail the relative positions of the microdose adapter/rotatable member 360, the male threaded proximal section 342 of the finger flange 340, and the plunger cap 370 one the microdose injection system 300 is in the vertical, or "de-bubbling," position. The threads on the male threaded proximal section 342 of the finger flange 340 have been omitted for clarity.

Figures 12, 13:
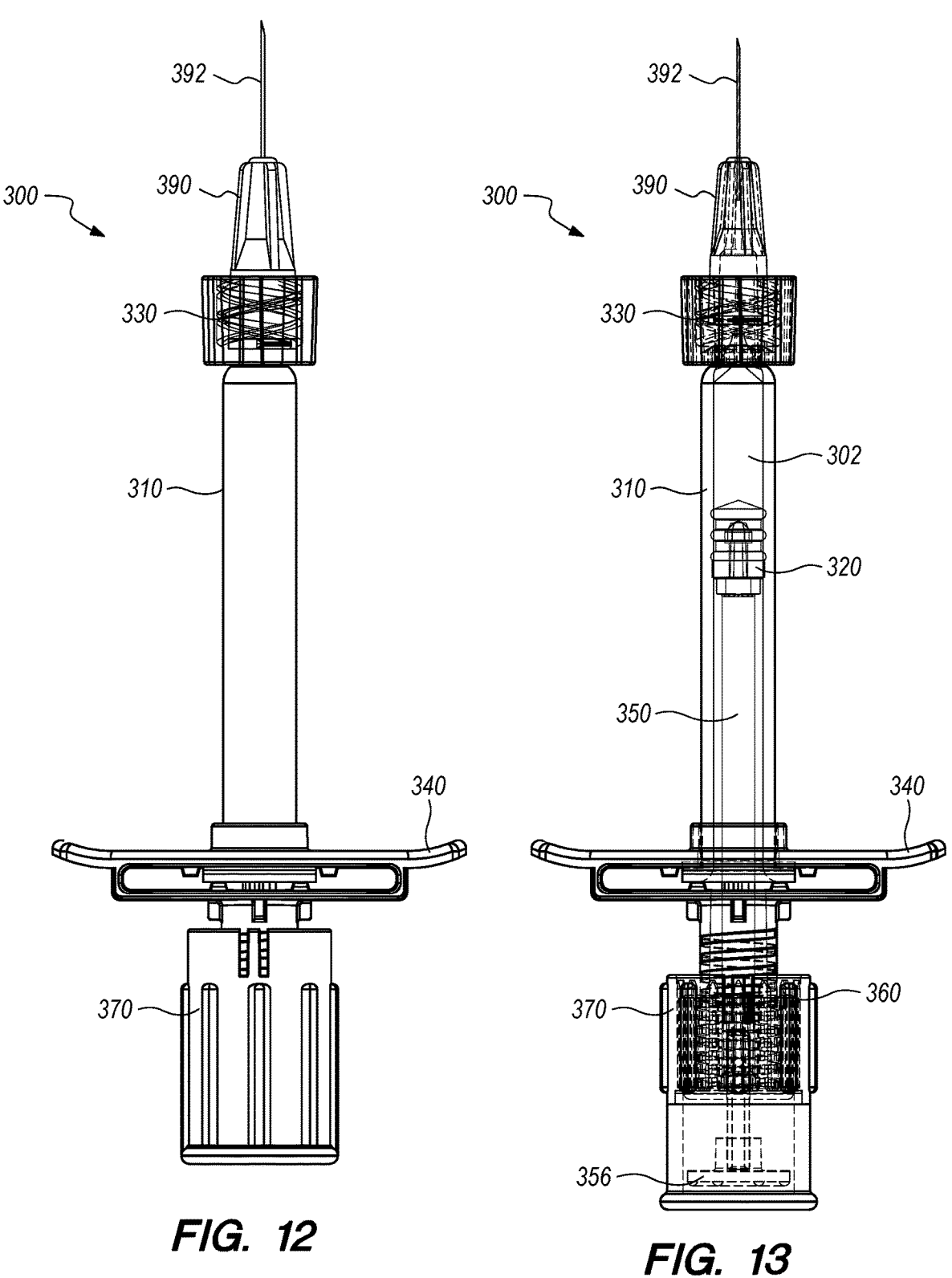
Figure 14:
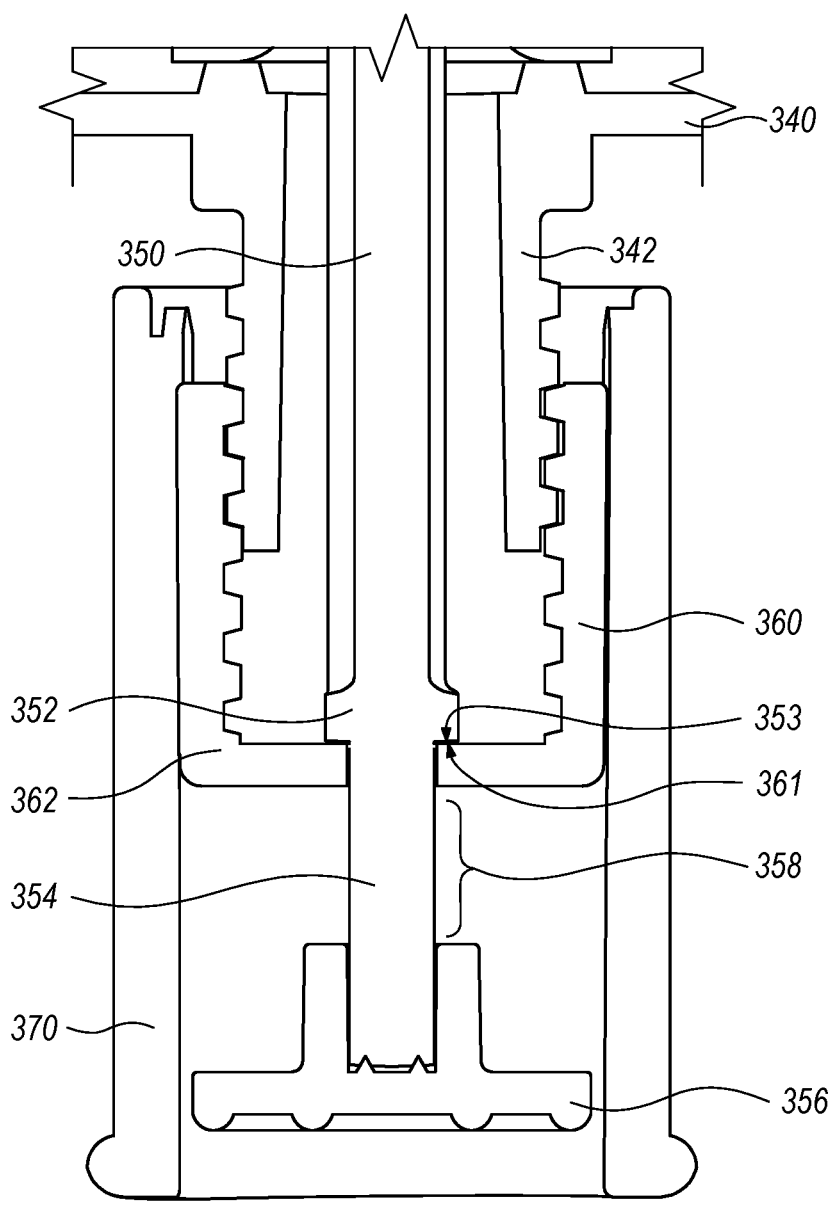

FIGS. 12-14 depict the microdose injection system 300 after the microdose injection system 300 has been de-bubbled. The de-bubbling process involves rotation of the microdose adapter/rotatable member 360 (e.g., in a clock-wise position for normal threaded parts) direction with the microdose injection system 300 in the vertical de-bubbling position.

Details regarding the microdose adapter/rotatable mem-ber 360 and the plunger cap 370 in the embodiment depicted in FIGS. 6-20 are described in U.S. patent application Ser. No. 16/011,453, the contents of which were previously fully incorporated herein by reference as though set forth in full. The plunger cap 370 has a plurality of internally directed splines and the microdose adapter/rotatable member 360 has a corresponding plurality of externally directed splines. The respective pluralities of internally and externally splines are configured such that when the plunger cap 370 is removably coupled to the plunger microdose adapter/rotatable member 360, rotation of the plunger cap 370 causes corresponding rotation of the microdose adapter/rotatable member 360.

Clockwise rotation of the microdose adapter/rotatable member 360 moves the microdose adapter/rotatable member 360 distally on the male threaded proximal section 342 of the finger flange 340, thereby advancing the plunger mem-ber 350 and the stopper member 320 coupled thereto distally in an interior of the syringe body 310. Moving the microdose adapter/rotatable member 360 distally relative to the syringe body 310 causes a distally facing surface 361 on the adapter 360 to exert a distally directed force on a proximally facing surface 353 on a shoulder/internal stop 352 coupled to or formed on a proximal end of the plunger member 350, as shown in FIG. 14. The distally directed force is proportional to the amount of rotation of the microdose adapter/rotatable member 360 and is delivered to the stopper member 320 through the plunger member 350.

The distally directed force moves the stopper member 320 distally in the interior of the syringe body 310. Because the microdose injection system 300 is in the vertical de-bubbling position, distal movement of the stopper member 320 in the interior of the syringe body 310 ejects the gas/air bubble (see 302 in FIG. 10) from the interior of the syringe body 310 and/or eject air from an interior of the needle assembly 390/needle 392, thereby de-bubbling or priming the microdose injection system 300.

Figures 15, 16:
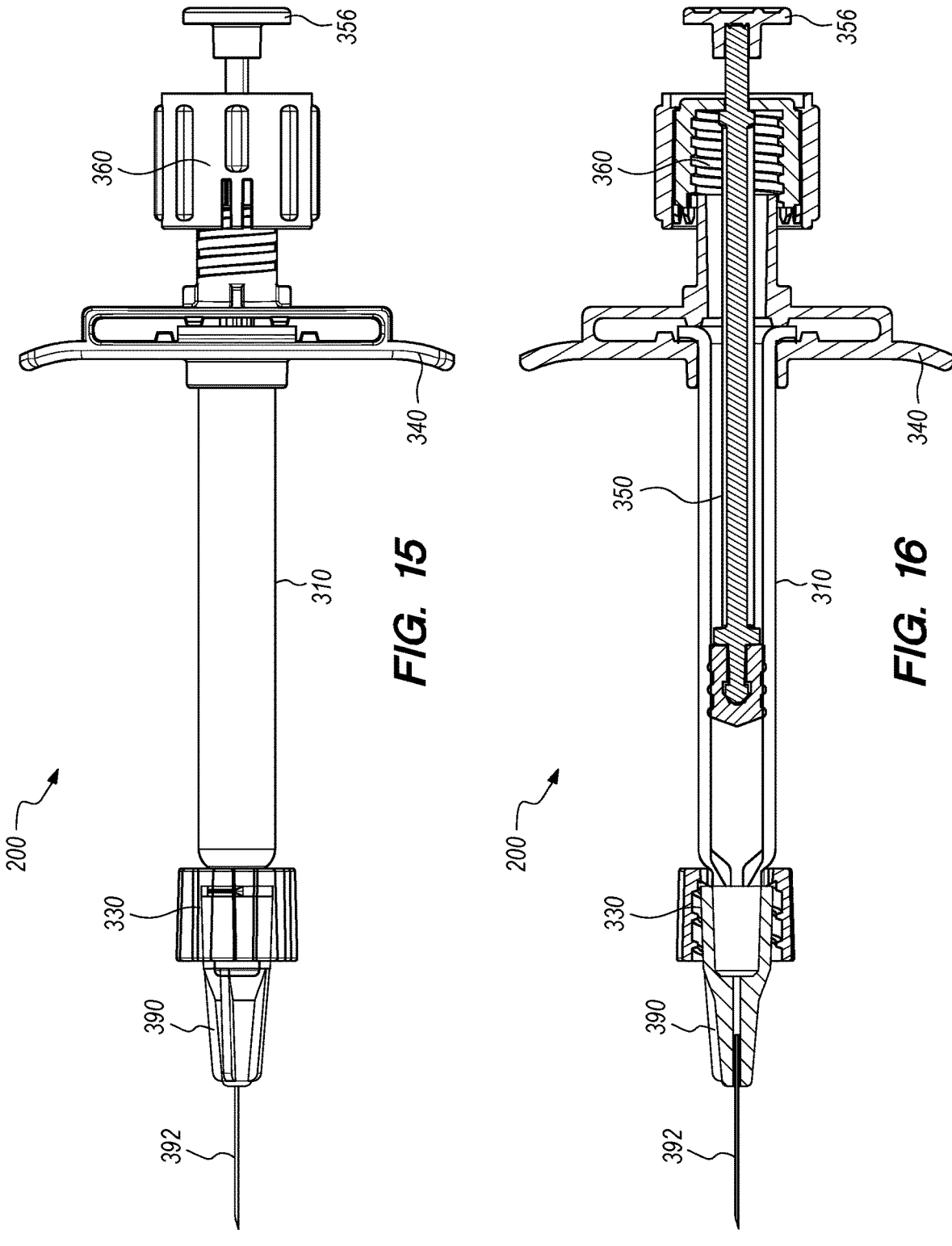
Figure 17:
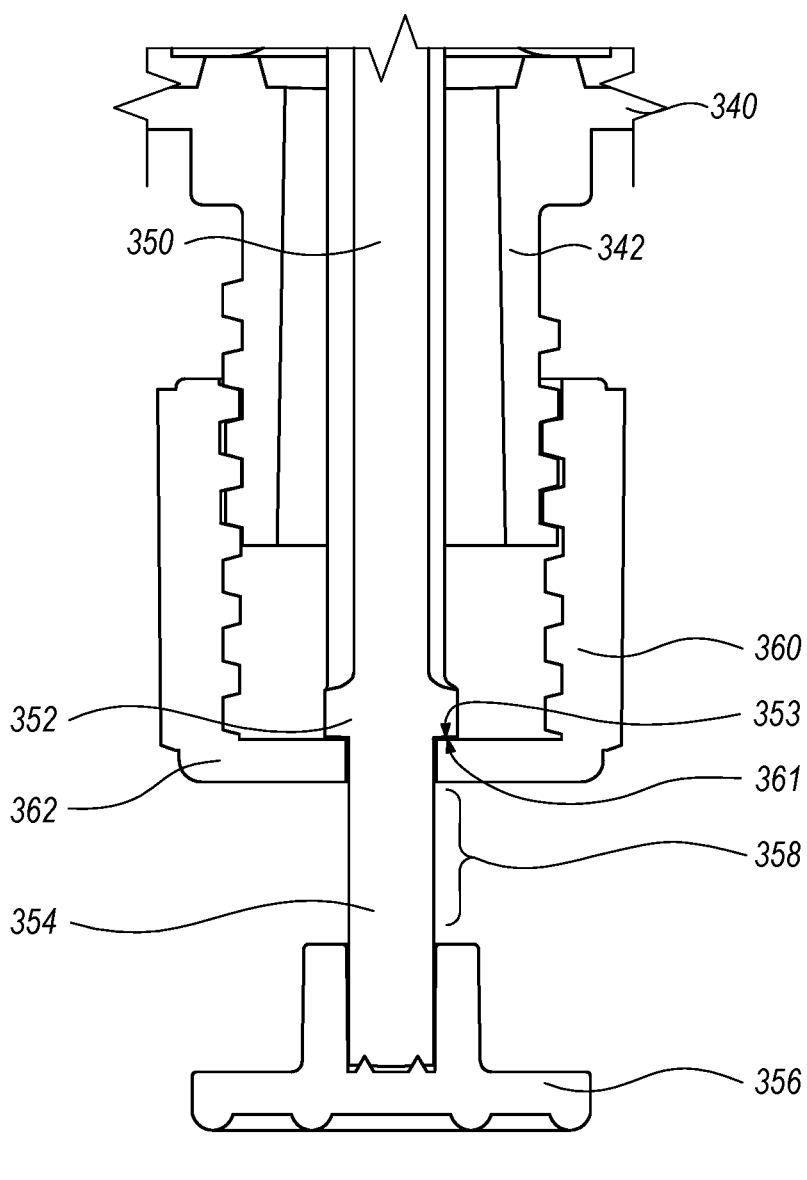

FIGS. 15-17 depict the next step in the injection process, which is removal of the plunger cap 370. By applying sufficient proximally directed force to the plunger cap 370, the elasticity of the retention members in the embodiment depicted in FIGS. 6-20 is overcome, and the plunger cap 370 can be moved proximally from the microdose adapter/rotatable member 360. Removal of the plunger cap 370 allows distal movement of the thumb pad/external stop 356 and the plunger member 350, thereby placing the microdose injection system 300 in a ready for injection state.

As shown in FIG. 17, the microdose adapter/rotatable member 360 includes a proximal flange 362. A narrow portion 354 of the plunger member 350 defines a gap 358 between a proximally facing surface of the proximal flange 362 and a distally facing surface of the thumb pad/external stop 356. The size of the gap 358 can be modified by modifying the plunger member 350 and/or the thumb pad/external stop 356. The size/axial length of the gap 358 determines the amount of axial movement of the stopper member 320 in the interior of the syringe body 310, and therefore the amount of fluid (e.g., medicine) injected by the microdose injection system 300.

Still referring to FIG. 17, the plunger member 350 also includes a shoulder/internal stop 352. The shoulder/internal stop 352 and the thumb pad/external stop 356 are sized such that neither of them can pass through the opening in the microdose adapter/rotatable member 360. Accordingly, the relative positions of the shoulder/internal stop 352 and the thumb pad/external stop 356 define the maximum travel of the plunger member 350 relative to the microdose adapter/rotatable member 360. This maximum travel of the plunger member 350 also corresponds to the size/axial length of the gap 358. The shoulder/internal stop 352 also prevents removal of the plunger member 350 from the microdose adapter/rotatable member 360.

Figures 18, 19:
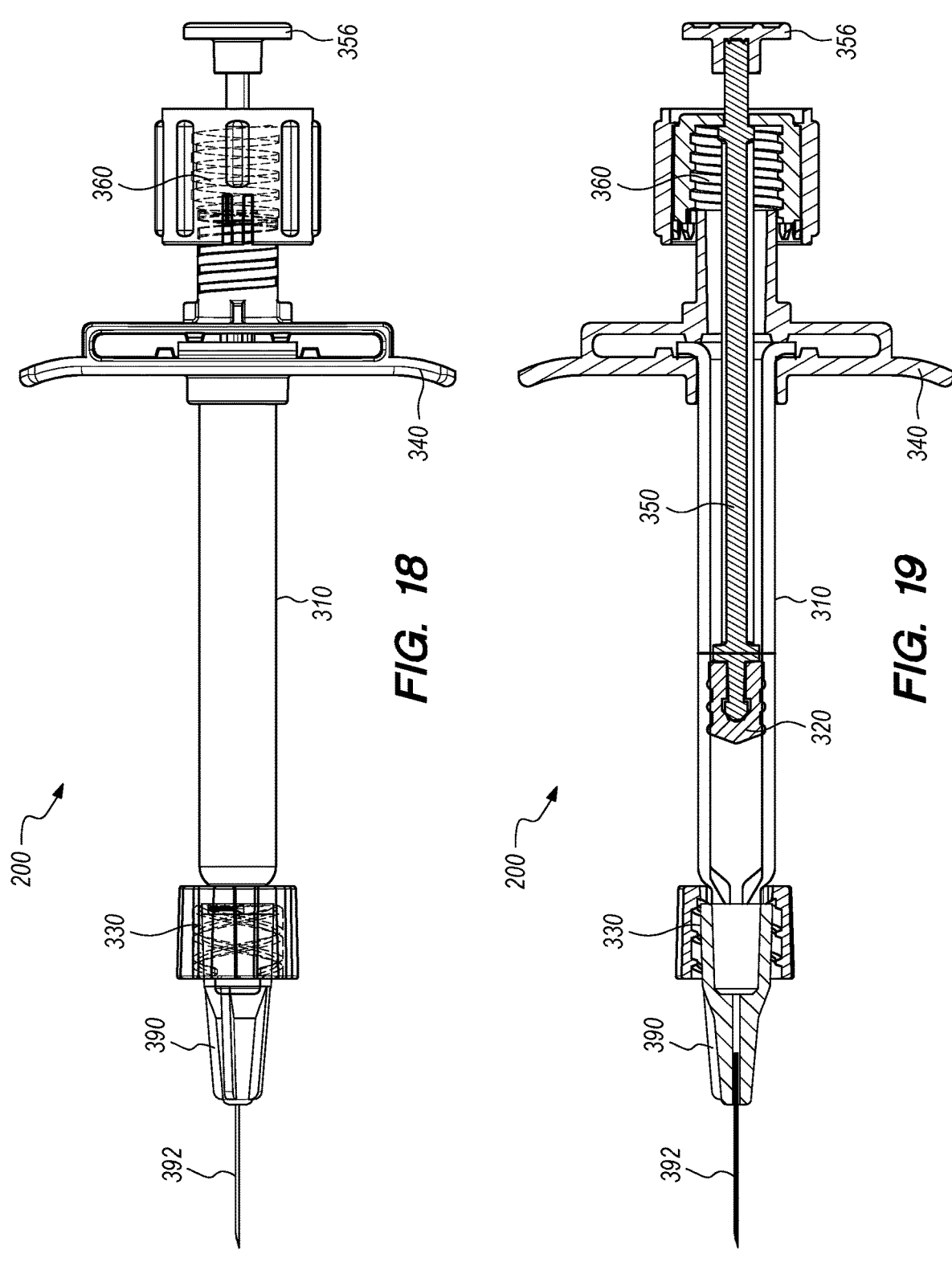
Figure 20:
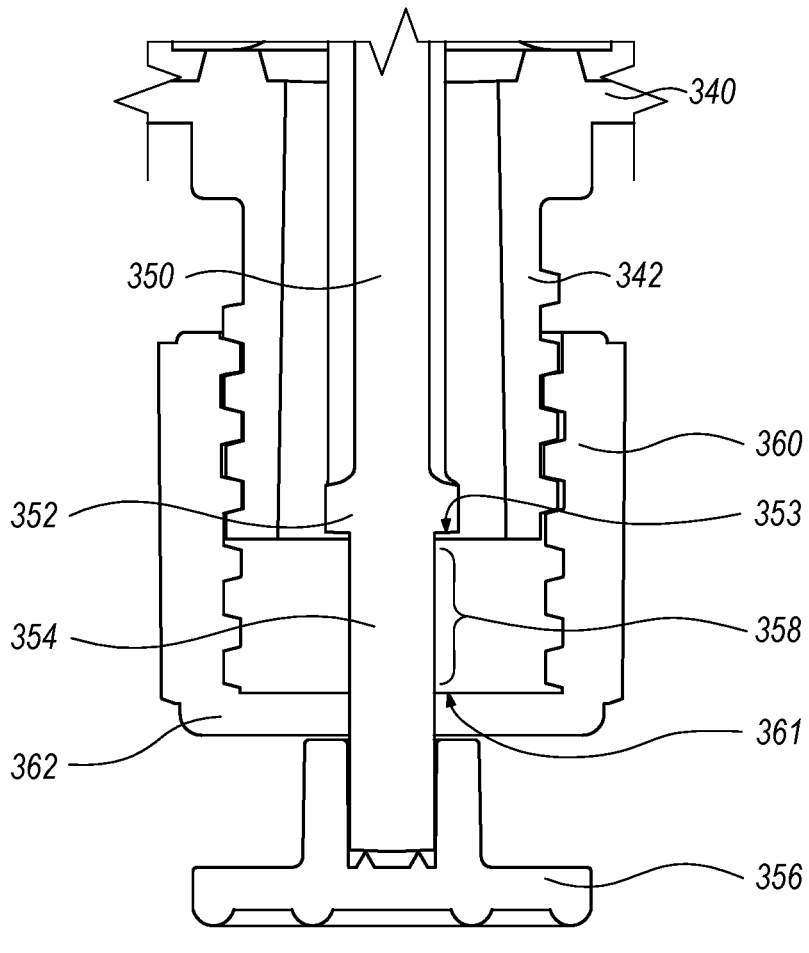

FIGS. 18-20 depict the next step in the injection process, which is giving the microdose injection. The distally directed force is applied to the thumb pad/external stop 356, thereby advancing the plunger member 350 and the stopper member 320 coupled thereto distally in an interior of the syringe body 310. The distally directed force can be applied manually by a user or automatically by an auto injector.

Comparing FIGS. 17 to 20 shows that application of the distally directed force to the thumb pad/external stop 356 collapses the gap 358 (see FIG. 17) outside of the microdose adapter/rotatable member 360. This also moves the shoulder/internal stop 352 distally away from the distal facing surface 361 of the microdose adapter/rotatable member 360. In fact, and internal gap 358' is now formed inside of the microdose adapter/rotatable member 360, as shown in FIG. 20. This internal gap 358' is the same size/axial length as the original gap 358 outside of the microdose adapter/rotatable member 360.

Comparing FIGS. 16 and 19 shows that distal movement of the stopper member 320 an interior of the syringe body

310 has ejected some fluid from the interior of the syringe body 310, resulting in an injection of a predetermined amount of fluid. In microdose applications, this predetermined amount of fluid can be from about 5 μL to about 250 μL. In one particular embodiment, this predetermined amount of fluid is about 10 μL.

Exemplary Plunger Cap/Rotatable Member Embodiment

FIGS. 21-29 depict a microdose injection system 400 according to some embodiments. The microdose injection system 400 is similar in structure and function to the system 300 depicted in FIGS. 6-20. However, the microdose injection system 400 includes a finger flange 440, a microdose adapter/rotatable member 460, and a plunger cap 470 that differ from the corresponding components 340, 360, 370 of the system 300 depicted in FIGS. 6-20.

The microdose injection system 400 includes a syringe body 410, a stopper member 420, a connection member 430, a finger flange 440, a plunger member 450, a needle assembly 490, a microdose adapter/rotatable member 460, and a plunger cap 470. Many of these system components (e.g., the syringe body 410, the stopper member 420, and the connection member 430) may be off-the-shelf components to utilize the existing and relatively well-controlled supply chain, and the corresponding assembly machinery and personnel. For instance, an off-the-shelf stopper member 420 refers to a commercially available stopper member, which has a generally smooth distally facing surface which contains no projections or recesses for coupling to a needle.

Figure 29:
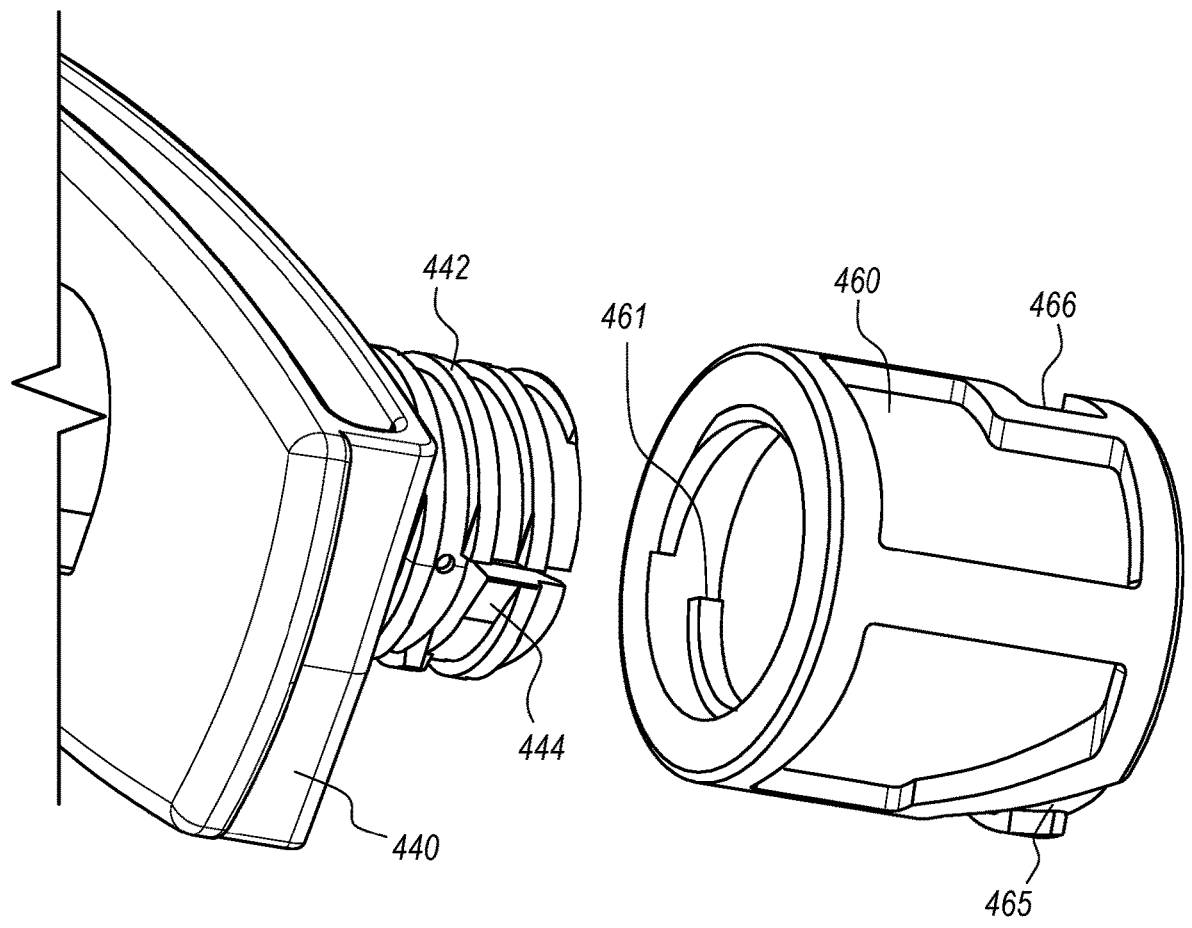

Like the finger flange 340 in the system 300 depicted in FIGS. 6-20, the finger flange 440 is removably coupleable to the syringe body 410 and includes a male threaded proximal section 442 configured to mate with the microdose adapter/rotatable member 460 having corresponding female threads. As shown in FIG. 29, the male threaded proximal section 442 includes a latch 444 configured to interfere with an end 461 of the female threads on the microdose adapter/rotatable member 460 to allow clockwise rotation of the microdose adapter/rotatable member 460 onto the male threaded proximal section 442 of the finger flange 440 while preventing counterclockwise rotation of the microdose adapter/rotatable member 460 past the latch 444. As such, the latch 444 prevents removal of the microdose adapter/rotatable member 460 from the finger flange 440 after it has been coupled to the finger flange 440. The adapter/rotatable member 460 may include inwardly projecting ribs (not shown) to engage with the latch 444 to provide multiple stop points spaced around the interior circumference to minimize backlash while preventing counterclockwise rotation. Additionally, the inwardly projecting ribs may be configured to provide tactile or audible feedback to the operator.

Figure 21:
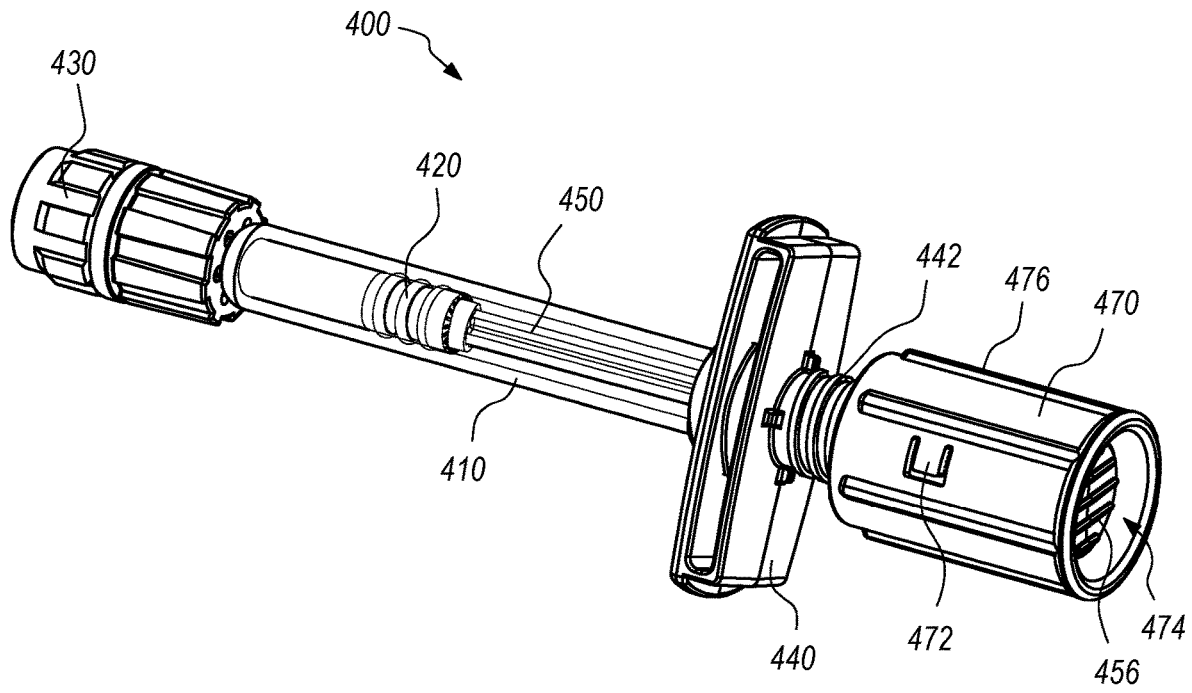
FIGS. 21-32 illustrate various aspects of microdose injection systems some with plunger caps and microdose injection methods according to some embodiments.
Figure 22:
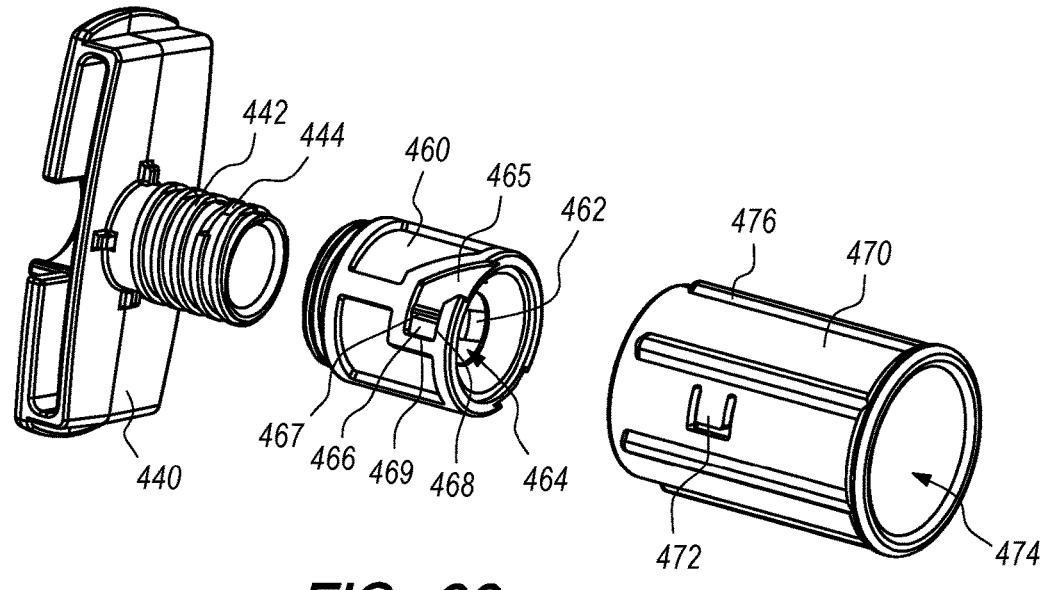
Figure 26:
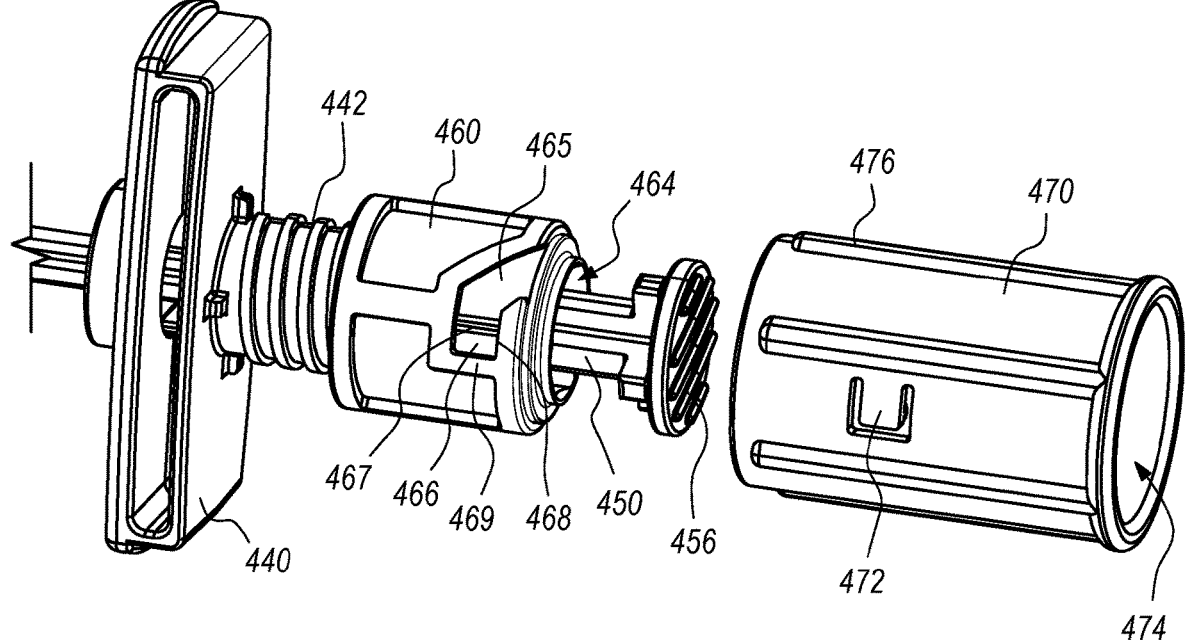
Figure 27:
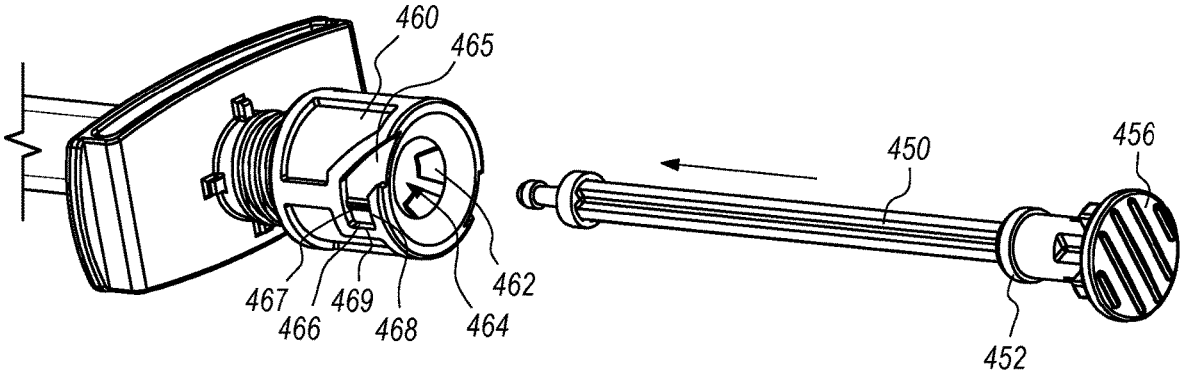
Figure 28:
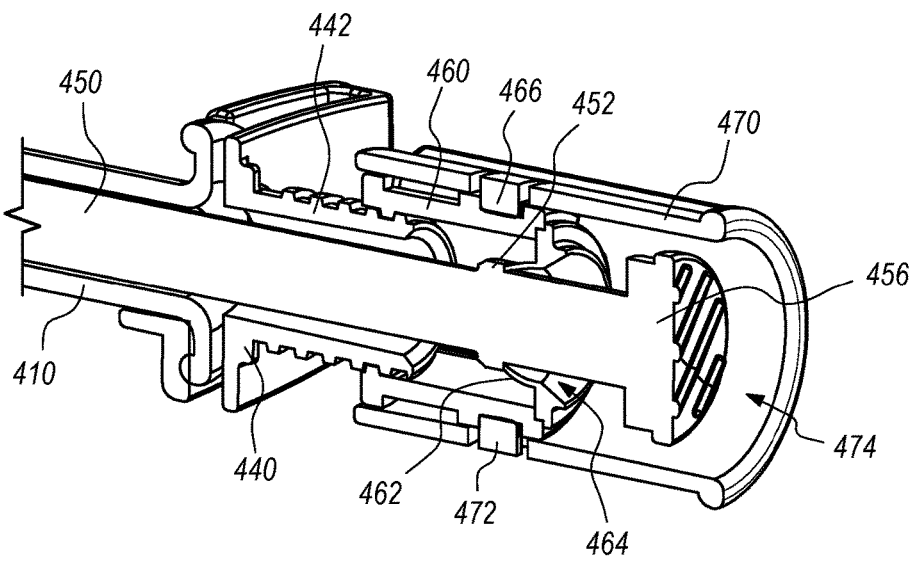

As shown in FIGS. 22, 27, and 28, the microdose adapter/rotatable member 460 includes a plurality of elastic latches 462 disposed around a central opening 464 and directed inwardly toward a longitudinal axis of the microdose adapter/rotatable member 460. In the embodiment depicted in FIGS. 21-29, the microdose adapter/rotatable member 460 includes for elastic latches 462. The elastic latches 462 are configured to interfere with a shoulder/internal stop 452 on the plunger member 450 to allow insertion of the plunger member 450 through the central opening 464 in the distal direction relative to the microdose adapter/rotatable member 460, while preventing removal of the plunger member 450 from the microdose adapter/rotatable member 460 after the former has been inserted through the latter.

The microdose adapter/rotatable member 460 also includes a pair of troughs on an exterior surface thereof. Each of the pair of troughs includes a slanted/diagonal trough 465 is open in a proximal direction at a proximal end to allow entry of components of the plunger cap 470 into the slanted/diagonal trough 465. The distal end of the slanted/ diagonal trough 465 connects to a circumferential trough 466. The circumferential trough 466 includes a bump 467 and a proximal surface 468 configured to removably couple the plunger cap 470 to the microdose adapter/rotatable member 460. The circumferential trough 466 also includes a circumferential surface 469 configured (along with the bump 467) to allow the plunger cap 470 to rotate the microdose adapter/rotatable member 460. Rotating the microdose adapter/rotatable member 460 in a clockwise direction moves the microdose adapter/rotatable member 460 in a distal direction. Because of the interference between the elastic latches 462 and the shoulder/internal stop 452 of the plunger member 450, moving the microdose adapter/ rotatable member 460 in a distal direction also moves the plunger member 450 (and the stopper member 420 attached thereto) in the distal direction.

As shown in FIG. 28, the plunger cap 470 includes a pair of elastic fingers 472 disposed on an interior surface thereof. The pair of elastic fingers 470 are configured to interfere with the corresponding pair of troughs 465, 466 and the bump 467 to removably couple the plunger cap 470 to the microdose adapter/rotatable member 460. The elastic fingers 472 are also configured to interfere with the circumferential surfaces 469 and the bumps 467 of the corresponding circumferential troughs 466 to allow the plunger cap 470 to rotate the microdose adapter/rotatable member 460. The interference between the elastic fingers 472 and the bumps 467 allows the plunger cap 470 to rotate the microdose adapter/rotatable member 460 in a clockwise direction to advance the plunger member 450 distally. After the microdose adapter/rotatable member 460 has been rotated to the limit of its travel in a clockwise direction, continued clockwise rotation of the plunger cap 470, moves the elastic fingers 472 past the bumps 467 in the circumferential troughs 466 and into the slanted/diagonal troughs 465. Continued clockwise rotation of the plunger cap 470, causes the elastic fingers 472 to follow the slanted/diagonal troughs 465 pushing the plunger cap 470 off of the adapter/rotatable member 460 at which the elastic fingers 472 can disengage from the slanted/diagonal troughs 465 thereby releasing the plunger cap 470 from the microdose adapter/rotatable member 460.

The plunger member 450 includes a thumb pad/external stop 456 at a distal end thereof to facilitate user application of distally directed force onto the plunger member 450 to perform the microdose injection. The plunger cap 470 also includes an axial window 474 that allows the thumb pad/ external stop 456 to be seen through the plunger cap 470 even when it is removably coupled to the microdose adapter/ rotatable member 460. By allowing the user to see the thumb pad/external stop 456, the axial window 474 help avoid the situation where a user believes that the plunger cap 470 is a thumb pad and applies distally directed force thereto. Although the plunger cap 470 cannot press distally on the actual thumb pad/external stop 456, application of distally directed force to the plunger cap 470 may damage the plunger cap 470. The axial opening 474 is sized and shaped to prevent manual manipulation of the thumb pad/external stop 456 from outside of the plunger cap 470. The plunger cap 470 also includes a knurled outer surface 476 to facilitate rotation thereof.

FIGS. 22-25 depict various steps in assembly of a microdose injection system 400 according to some embodiments. In FIG. 22, the finger flange 440, the microdose adapter/ rotatable member 460, and the plunger cap 470 are positioned for assembly. The microdose adapter/rotatable member 460 is rotated clockwise onto the proximal section 442 of the finger flange 440. The microdose adapter/rotatable member 460 is rotated onto the finger flange 440 until the latch 444 on the finger flange 440 engages with the microdose adapter/rotatable member 460. Then the plunger cap 470 is rotated counterclockwise onto the microdose adapter/ rotatable member 460 by aligning the pair of elastic fingers 472 with the proximal opening to the corresponding pair of slanted/diagonal troughs 465 on the microdose adapter/ rotatable member 460. The plunger cap 470 is rotated onto the microdose adapter/rotatable member 460 until the elastic fingers 472 past the bumps 467 in the circumferential troughs 466, thereby temporarily securing the plunger cap 470 onto the microdose adapter/rotatable member 460.

Figure 23:
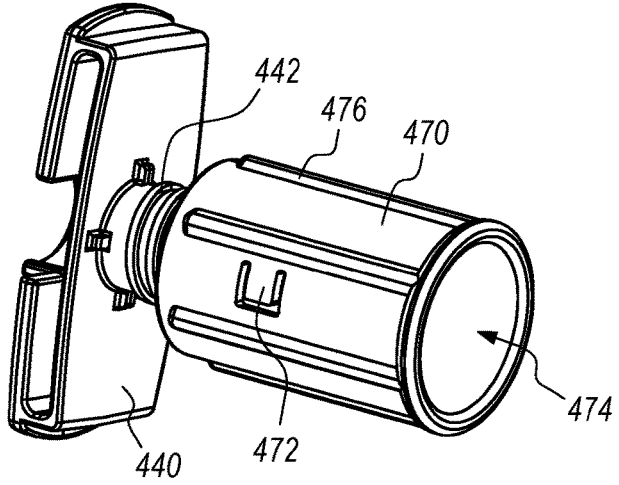
Figure 24:
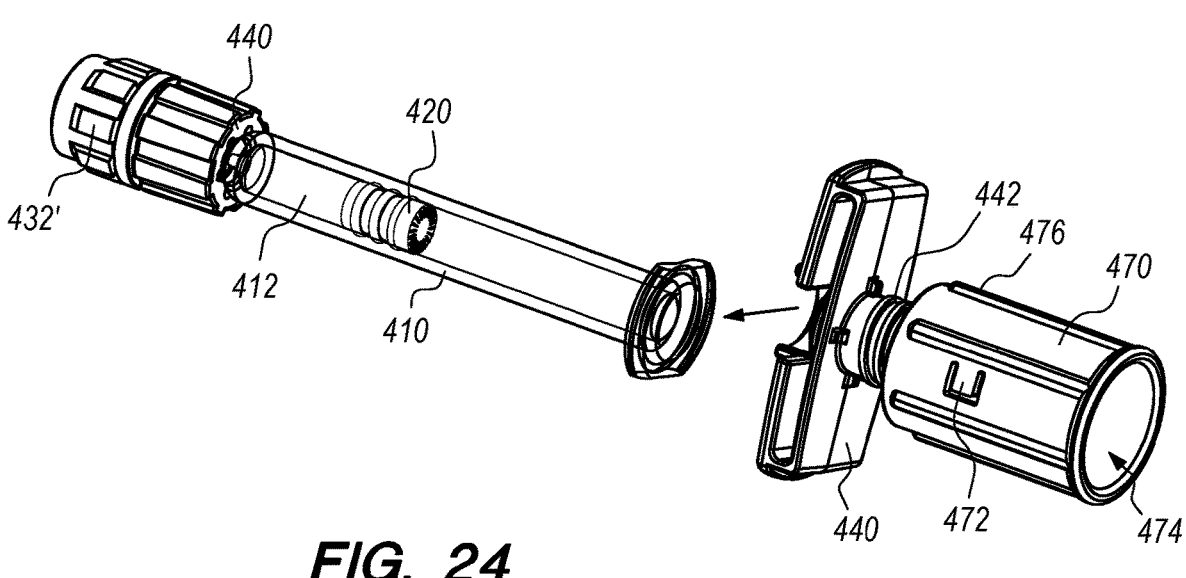

FIG. 23 depicts the result of assembling the finger flange 440, the microdose adapter/rotatable member 460, and the plunger cap 470. FIG. 24, depicts the next step in which the assembled finger flange 440, microdose adapter/rotatable member 460, the plunger cap 470 are removably coupled to the glass syringe flange of a syringe body 410. A lateral opening in the finger flange 440 is slid over the syringe flange of the syringe body 410 to removably couple the finger flange 440 to the syringe body 410. The syringe body 410 may be constructed of glass, polymer (such as COC, COP, polypropylene, polyester or other polymeric materials), metal or other suitable material. The syringe body may be configured with a user removable connection member cap 432' for later attachment of a needle or may have a preattached needle (not shown). The syringe body 410 may be pre-filled with medicine 412 and closed with a syringe cap and stopper member 420 prior to assembly of the flange and plunger member. Pre-filling of the syringe body 410 occurs in an aseptic filling machine. By assembling the finger flange and plunger member after prefilling of the syringe the filling machine mechanisms necessary for finger flange attachment is not needed inside the aseptic filling machine, allowing for faster filling machine throughput and a less costly aseptic filling machine.

Figure 25:
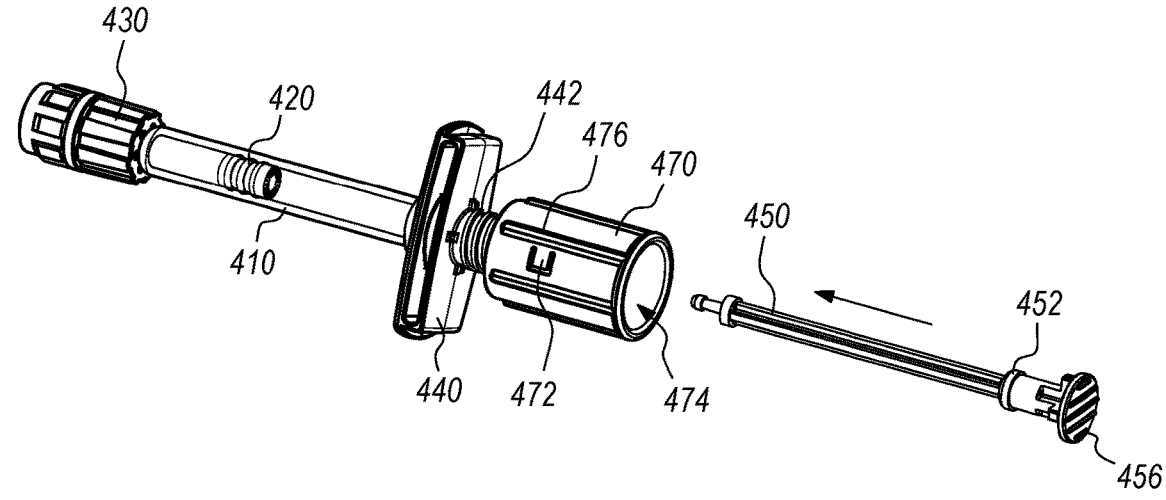

FIG. 25 depicts insertion of the plunger member 450 through the proximal opening 474 in the plunger cover 470, the central opening 464 in the microdose adapter/rotatable member 460 and the finger flange 440, and into the syringe body 410. The plunger member 450 is inserted until the shoulder/internal stop 452 thereon moves distally past the elastic latches 462 on the microdose adapter/rotatable member 460, which prevents proximal withdrawal of the plunger member 450 out of the microdose adapter/rotatable member 460.

After insertion of the plunger member 450 into the syringe body 410, the distal end of the plunger member 450 is coupled to the stopper member 420 (e.g., by rotating the plunger member 450 onto the stopper member 420 through the proximal opening 474 in the plunger cap 470). Coupling the plunger member 450 to the stopper member 420 completes the assembly process resulting in a ready to use microdose injection system 400, as shown in FIG. 21. The coupling of the plunger member 450 to the stopper member 420 may occur simultaneous to the shoulder 452 being inserted past the elastic latches 462. Alternatively, the coupling of the plunger member 450 may occur before or after the insertion of the shoulder 452 past the elastic latches 462. In another embodiment, there are no threads on the end of the plunger member 450. Instead, there is a bump that snaps into a socket in the stopper member 420. In yet another embodiment, there is a pin at the end of the plunger member 450 to maintain alignment during engagement with the stopper member 420.

FIG. 26 depicts an intermediate step in assembly of a microdose injection system 400 according to some alternative embodiments. In this embodiment, the microdose adapter/rotatable member 460 is rotated onto the finger flange 440, which is then removably coupled to the syringe flange on the syringe body 410. Next the plunger member 450 is inserted through the central opening 464 in the microdose adapter/rotatable member 460 and the finger flange 440, and into the syringe body 410. Then the distal end of the plunger member 450 is coupled to the stopper member 420 (e.g., by rotating the plunger member 450 onto the stopper member 420). Finally, the plunger cap 470 is rotated onto the microdose adapter/rotatable member 460 to complete assembly of the microdose injection system 400. The insertion of the plunger member 450 into the adapter/rotatable member 460 may occur with the plunger cap 470 in place on the adapter/rotatable member 460 or prior to the plunger cap 470 assembly onto the adapter/rotatable member 460. FIG. 27 shows insertion of the plunger member 450 into the central opening 464 of the microdose adapter/rotatable member 460.

Figure 30:
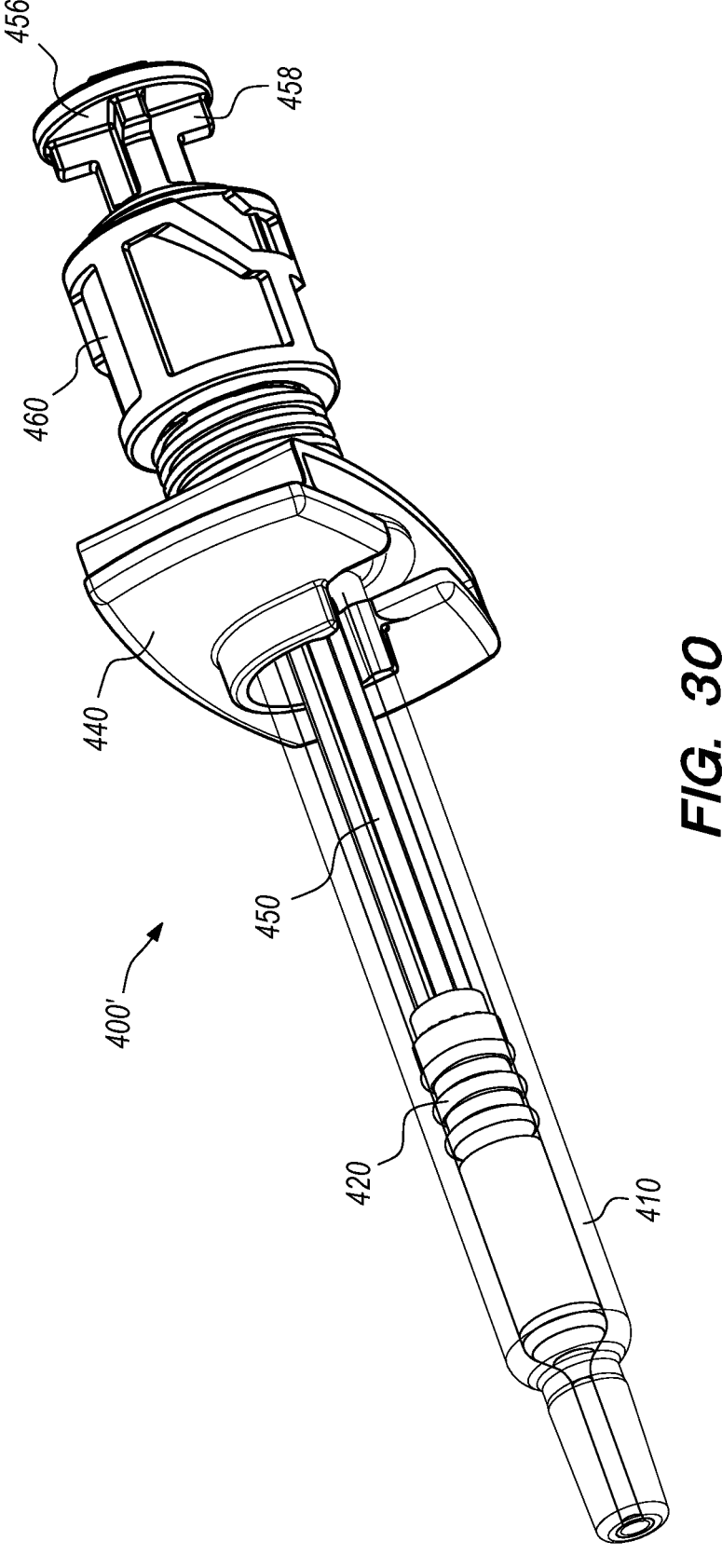
Figure 31:
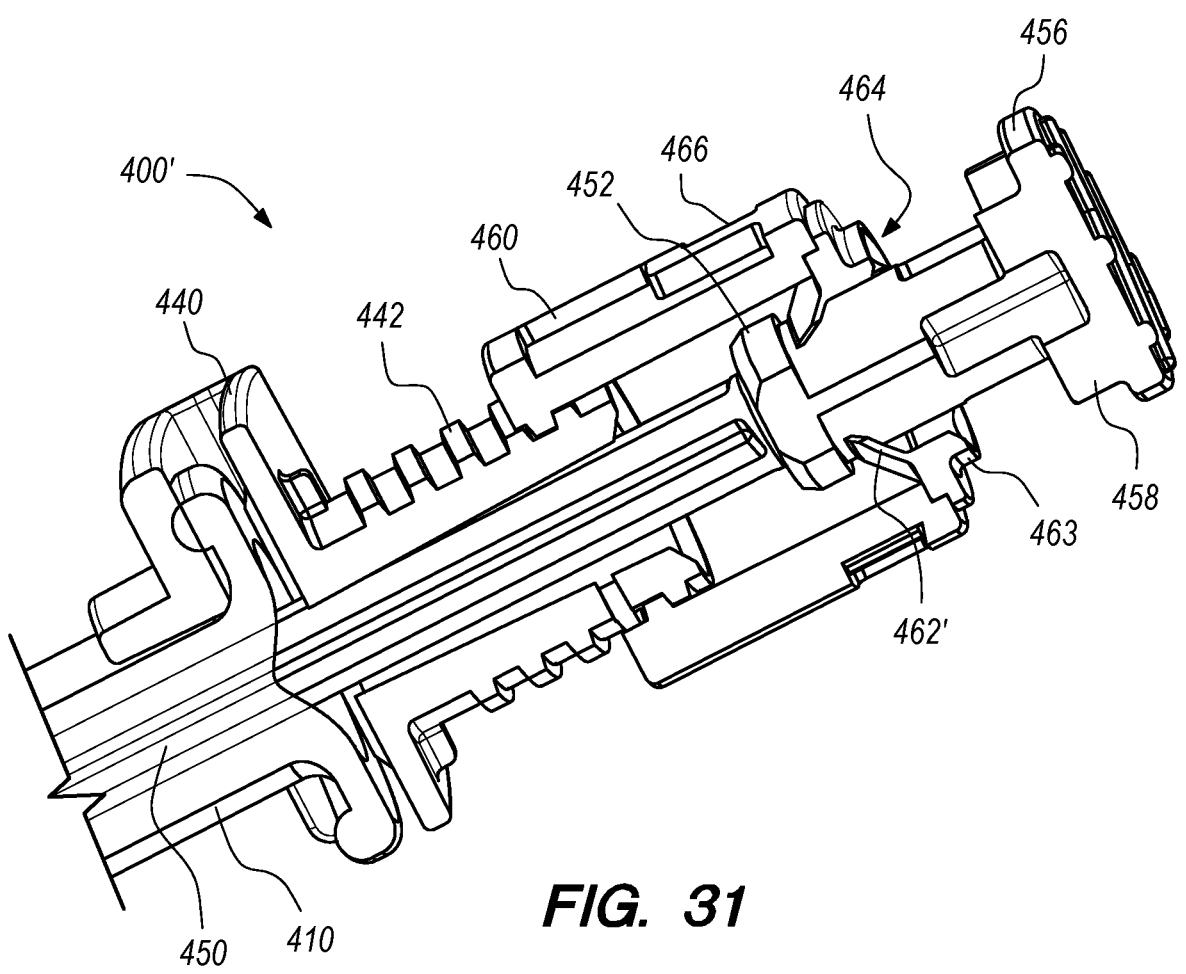
Figure 32:
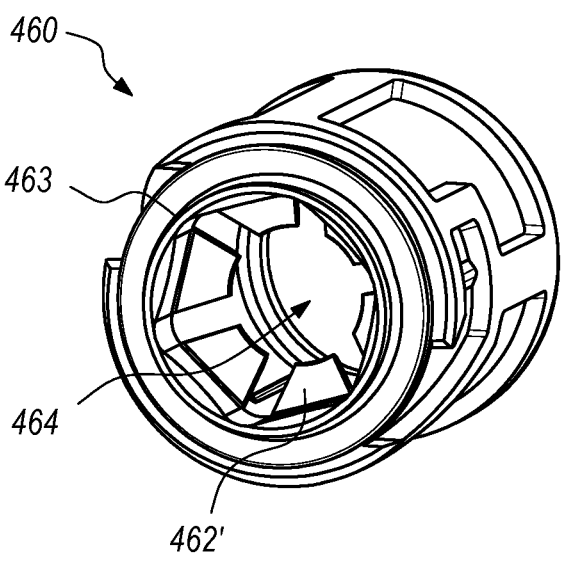

FIGS. 30-32 depict a microdose injection system 400' according to some embodiments. The microdose injection system 400' is similar in structure and function to the microdose injection system 400 depicted in FIGS. 21-29. For instance, the microdose injection system 400' shown in FIG. 30 includes a syringe body 410, a stopper member 420, a finger flange 440, a plunger member 450, and a microdose adapter/rotatable member 460'. The system 400' also includes a connection member, a needle assembly, a removable connection member cap, and a plunger cap, as depicted in FIGS. 21-29 and described above. However, these components are omitted for clarity.

One difference between the microdose injection systems 400, 400' depicted in FIGS. 21-29 and 30-32 is the number of elastic latches 426, 426'. The microdose injection system 400 depicted in FIGS. 21-29 has four elastic latches 426 while the microdose injection system 400' depicted in FIGS. 30-32 has six elastic latches 426' (see FIG. 32).

Another difference between the microdose injection systems 400, 400' depicted in FIGS. 21-29 and 30-32 is the shape of the proximally extending flange 463 at the proximal end of the microdose adapter/rotatable member 460'. The microdose injection system 400 depicted in FIGS. 21-29 has a slanted flange (see FIG. 28) while the microdose adapter/rotatable member 460' depicted in FIGS. 30-32 has a vertical flange 463 (see FIGS. 31 and 32). The flange 463 on the microdose adapter/rotatable member 460' interferes with the external stop 458 on the distal face of the thumb pad 456 to limit distal movement of the plunger member 450 and to define the size of a dose for injection. This interference is accomplished with elastic finger style latches 462' as shown in FIG. 30-32, but may be accomplished with other mechanical interference mechanisms such as a ratchet/pawl, snap fit, press fit, clutch, toothless friction ratchet, or other mechanical coupling mechanisms.

While various embodiments have been described with specific connectors (e.g., slip and Luer), these embodiments can be used with any known injection system connectors. While various embodiments have been described with staked needles and needle connectors, these embodiments can be used with any known permanently coupled needle or needle connector system.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, PTFE, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A method for assembling a system for injecting, the method comprising:

coupling a rotatable member to a finger flange to form a finger flange/rotatable member unit;

mounting the finger flange/rotatable member unit onto a pre-filled syringe, wherein the pre-filled syringe comprises a syringe body defining a syringe interior, an injectable fluid disposed in the syringe interior, and a stopper member disposed in the syringe interior and retaining the injectable fluid in the syringe interior;

inserting a plunger member through the finger flange/rotatable member unit into the syringe interior; and coupling the plunger member to the stopper member in the syringe interior, further comprising coupling a plunger cap to the rotatable member to form a finger flange/rotatable member/plunger cap unit, wherein the finger flange comprises a side opening, and wherein the syringe body comprises a syringe flange, the method further comprising mounting the finger flange/rotatable member/plunger cap unit onto the syringe body by inserting the syringe flange of the syringe body into the side opening of the finger flange.

2. The method of claim 1, wherein the finger flange comprises a proximally directed screw, the method further comprising coupling the rotatable member to the finger flange to form the finger flange/rotatable member unit by twisting the rotatable member onto the proximally directed screw on the finger flange.

3. The method of claim 1, wherein the plunger cap defines a proximal opening, wherein the rotatable member defines a rotatable member opening, and wherein the finger flange defines a finger flange opening, the method further comprising inserting the plunger member through the proximal opening, the rotatable member opening, and the finger flange opening into the syringe interior.

4. The method of claim 3, wherein wherein the rotatable member defines a slanted trough and a circumferential trough on an exterior surface thereof, and wherein the plunger cap comprises a tang inwardly directed toward a longitudinal axis of the plunger cap, the method further comprising coupling the plunger cap to the rotatable member to form the finger flange/rotatable member/plunger cap unit by twisting the plunger cap onto the rotatable member such that the tang in the plunger cap is disposed in the circumferential trough and an interference between the tang and the circumferential trough prevents proximal movement of the plunger cap relative to the rotatable member.

5. The method of claim 1, wherein the stopper member comprises a threaded stopper member recess, and wherein the plunger member comprises a distal threaded member, the method further comprising coupling the plunger member to the stopper member in the syringe interior by twisting the distal threaded member of the plunger member into the threaded stopper member recess of the stopper member.

6. A method for injecting a fluid, comprising:

providing a syringe assembly, the syringe assembly comprising a syringe body having proximal and distal ends, a syringe interior, a distal needle interface at the distal end thereof, and a syringe flange at the proximal end thereof, an injectable fluid disposed in the syringe interior, a stopper member disposed in the syringe interior, a plunger member coupled to the stopper member, a finger flange removably coupled to the syringe flange, the finger flange including a proximally directed screw, a rotatable member disposed on the proximally directed screw, a plunger cap removably coupled to the rotatable member, and a needle assembly having a needle coupled to the distal needle interface of the syringe body;

rotating the plunger cap relative to the proximally directed screw to rotate the rotatable member relative to the proximally directed screw to thereby force a portion the injectable fluid from the syringe interior through the needle to prime the needle for injection;

removing the plunger cap from the rotatable member to thereby expose a proximal end of the plunger member; and applying a distally directed force to the proximal end of the plunger member to expel another portion of the injectable fluid from the syringe interior through the needle.

7. The method of claim 6, wherein the rotatable member defines a slanted trough and a circumferential trough on an exterior surface thereof and includes a bump disposed on the exterior surface thereof between the slanted trough and the circumferential trough, wherein the plunger cap comprises a tang inwardly directed toward a longitudinal axis of the plunger cap, wherein when the tang is disposed in the circumferential trough, an interference between the tang and the circumferential trough prevents proximal movement of the plunger cap relative to the rotatable member, and wherein the bump on the rotatable member and the tang on the plunger cap are configured to prevent the plunger cap from disengaging from the rotatable member until a predetermined amount of torque is applied to the plunger cap relative to the rotatable member.

8. The method of claim 7, wherein removing the plunger cap from the rotatable member comprises applying the predetermined amount of torque to the plunger cap relative to the rotatable member after the rotatable member reaches a distal end of the proximally directed screw on the finger flange.

\* \* \* \* \*